United States Patent [19]

Roch et al.

[11] Patent Number: 4,478,833
[45] Date of Patent: Oct. 23, 1984

[54] TRISUBSTITUTED PYRIMIDO[5,4-D]PYRIMIDINES AND SALTS THEREOF

[75] Inventors: Josef Roch; Erich Müller; Berthold Narr; Josef Nickl; Walter Haarmann; Johannes M. Weisenberger, all of Biberach, Fed. Rep. of Germany

[73] Assignee: Dr. Karl Thomae Gesellschaft mit beschränkter Haftung, Biberach an der Riss, Fed. Rep. of Germany

[21] Appl. No.: 331,285

[22] Filed: Dec. 16, 1981

[30] Foreign Application Priority Data

Dec. 27, 1980 [DE] Fed. Rep. of Germany ....... 3049207

[51] Int. Cl.³ ................. C07D 401/14; C07D 417/14; A61K 31/505; C07D 487/04
[52] U.S. Cl. .................................... 424/246; 424/251; 424/248.56; 424/248.57; 424/248.4; 260/243.3; 544/256; 544/118; 544/58.2; 544/61
[58] Field of Search ...................... 544/256, 118, 58.2, 544/61; 424/246, 248.56, 248.57, 248.4, 251; 260/243.3

[56] References Cited

U.S. PATENT DOCUMENTS

| 3,031,450 | 4/1962 | Fischer et al. | 544/256 |
| 3,074,928 | 1/1963 | Roch et al. | 544/118 |
| 3,322,755 | 5/1967 | Roch et al. | 260/246 |

FOREIGN PATENT DOCUMENTS

| 247048 | 11/1960 | Australia | 544/118 |
| 23559 | 2/1982 | European Pat. Off. | |
| 1150086 | 6/1963 | Fed. Rep. of Germany | 544/118 |
| 1292943 | 4/1962 | France | |
| 807826 | 1/1959 | United Kingdom | |
| 1051218 | 12/1966 | United Kingdom | |

Primary Examiner—John M. Ford
Attorney, Agent, or Firm—Hammond & Littell, Weissenberger & Dippert

[57] ABSTRACT

Compounds of the formula

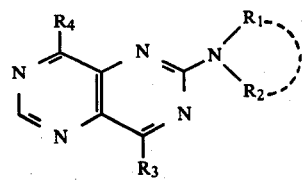

wherein
$R_1$ is optionally substituted alkyl;
$R_2$ is hydrogen or optionally substituted alkyl; or
$R_1$ and $R_2$, together with each other and the nitrogen atom to which they are attached, form an optionally substituted cyclic imino group;
$R_3$ is an optionally substituted cyclic imino group; and
$R_4$ is substituted hydroxyl, mercapto or amino;

and non-toxic, pharmacologically acceptable acid addition salts thereof. The compounds as well as their salts are useful as antithrombotics.

9 Claims, No Drawings

TRISUBSTITUTED PYRIMIDO[5,4-D]PYRIMIDINES AND SALTS THEREOF

This invention relates to novel trisubstituted pyrimido[5,4-d]pyrimidines and non-toxic acid addition salts thereof, to methods of preparing these compounds, to pharmaceutical compositions containing them as active ingredients, and to a method of using them as antithrombotics. More particularly, the present invention relates to a novel class of pyrimido[5,4-d]pyrimidines represented by the formula

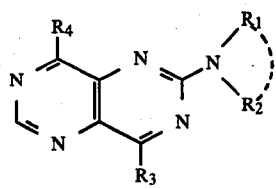

wherein $R_1$ is straight or branched alkyl of 2 to 8 carbon atoms, optionally substituted in the 2- to 8-position by up to 5 hydroxyls; alkyl of 2 to 4 carbon atoms monosubstituted in the 2-, 3- or 4-position by alkoxy of 1 to 3 carbon atoms, amino, (alkyl of 1 to 3 carbon atoms-)amino, di(alkyl of 1 to 3 carbon atoms)amino or morpholino; methyl; or pyridyl-methyl;

$R_2$ is hydrogen; alkyl of 1 to 3 carbon atoms; or alkyl of 2 to 3 carbon atoms mono-substituted in the 2- or 3-position by hydroxyl or alkoxy of 1 to 3 carbon atoms; or $R_1$ and $R_2$, together with each other and the nitrogen atom to which they are attached, are imidazolyl; morpholino; thiomorpholino; 1-oxido-thiomorpholino; piperidino; or mono-substituted piperidino, where the substituent is hydroxyl, alkoxy of 1 to 3 carbon atoms, hydroxy(alkyl of 1 to 3 carbon atoms), alkoxycarbonyl of 2 to 4 carbon atoms, amino, (alkanoyl of 1 to 3 carbon atoms)-amino, aminocarbonyl, (alkyl of 1 to 3 carbon atoms)-amino or di(alkyl of 1 to 3 carbon atoms)-amino;

$R_3$ is morpholino, thiomorpholino, 1-oxidothiomorpholino or 1,1-dioxido-thiomorpholino, each of which is optionally mono- or di-substituted by one or two alkyls of 1 to 3 carbon atoms;

$R_4$ is

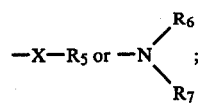

X is sulfur or oxygen;

$R_5$ is alkyl of 1 to 4 carbon atoms, optionally monosubstituted by phenyl or in the 2-, 3-or 4-position by hydroxyl, di(alkyl of 1 to 3 carbon atoms)-amino, alkoxy of 1 to 3 carbon atoms or alkoxycarbonyl of 2 to 4 carbon atoms; when X is sulfur, also phenyl; where each of the aforementioned phenyl moieties may optionally be methylenedioxy-substituted, mononitro-substituted, or mono- or di-substituted by alkyl of 1 to 3 carbon atoms, alkoxy of 1 to 3 carbon atoms, (alkyl of 1 to 3 carbon atoms)-thio, trifluoromethyl and/or halogen; alkyl of 5 to 8 carbon atoms; cycloalkyl of 5 to 7 carbon atoms; furfuryl; indanyl; or naphthylmethyl;

$R_6$ is hydrogen; alkyl of 1 to 4 carbon atoms; or alkyl of 2 to 4 carbon atoms monosubstituted in the 2-, 3- or 4-position by hydroxyl or alkoxy of 1 to 3 carbon atoms; and $R_7$ is hydrogen; alkyl of 1 to 4 carbon atoms; phenyl-(alkyl of 1 to 4 carbon atoms); phenyl; where each of the aforementioned phenyl moieties may optionally be methylenedioxy-substituted or mono- or di-substituted by alkyl of 1 to 3 carbon atoms, alkoxy of 1 to 3 carbon atoms, (alkyl of 1 to 3 carbon atoms)-thio, trifluoromethyl and/or halogen; alkyl of 5 to 8 carbon atoms; cycloalkyl of 5 to 7 carbon atoms; alkyl of 2 to 8 carbon atoms mono-substituted in the 2- to 8-position by hydroxyl, alkoxy of 1 to 3 carbon atoms or hydroxy-(alkoxy of 1 to 3 carbon atoms); cyclohexylmethyl; hydroxycyclohexyl; furfuryl; or pyridyl-methyl; or $R_6$ and $R_7$, together with each other and the nitrogen atoms to which they are attached, are alkyleneimino of 4 to 7 carbon atoms, optionally monohydroxy-substituted or mono- or di-substituted by alkyl of 1 to 3 carbon atoms; tetrahydropyridino; tetrahydroquinolino; or tetrahydroisoquinolino;

and non-toxic, pharmacologically acceptable acid addition salts thereof.

Specific examples of substituents $R_1$ through $R_4$ are the following:

$R_1$—methyl, ethyl, propyl, isopropyl, butyl, isobutyl, pentyl, isopentyl, neopentyl, hexyl, heptyl, octyl, 2-aminoethyl, 3-aminopropyl, 4-aminobutyl, 2-methylaminoethyl, 2-propylaminoethyl, 2-dimethylaminoethyl, 3-diethylaminopropyl, 4-methylethylaminobutyl, 2-morpholinoethyl, 2-hydroxyethyl, 3-hydroxypropyl, 4-hydroxybutyl, 5-hydroxypentyl, 6-hydroxyhexyl, 7-hydroxyheptyl, 8-hydroxyoctyl, 2-hydroxypropyl, 2,3-dihydroxypropyl, 3-hydroxy-2,2-dimethylpropyl, 2,3-dihydroxybutyl, 2,4-dihydroxybutyl, 2,3,4-trihydroxybutyl, 2,3,4,5-tetrahydroxypentyl, 2,3,4,5,6-pentahydroxyhexyl, 1,5-dimethyl-5-hydroxyhexyl, 2-methoxyethyl, 3-ethoxypropyl, 2-propoxyethyl, 4-methoxybutyl or pyridylmethyl.

$R_2$—methyl, ethyl, propyl, isopropyl, 2-hydroxyethyl, 2-hydroxypropyl, 3-hydroxypropyl, 2-methoxyethyl, 2-isopropoxyethyl, 3-methoxypropyl or 2-methoxypropyl.

$R_1$ and $R_2$, together with each other and the nitrogen atom to which they are attached—imidazolyl, morpholino, thiomorpholino, 1-oxido-thiomorpholino, piperidino, methyl-piperidino, ethyl-piperidino, dimethyl-piperidino, hydroxy-piperidino, methoxy-piperidino, ethoxy-piperidino, hydroxymethyl-piperidino, 2-hydroxyethyl-piperidino, methoxycarbonyl-piperidino, ethoxycarbonyl-piperidino, dimethylamino-piperidino, acetylamino-piperidino, propionylamino-piperidino or aminocarbonyl-piperidino.

$R_3$—morpholino, methyl-morpholino, propyl-morpholino, dimethyl-morpholino, ethylmethyl-morpholino, thiomorpholino, ethyl-thiomorpholino, 1-oxidothiomorpholino, 1,1-dioxido-thiomorpholino or methyl-1,1-dioxido-thiomorpholino.

$R_4$—methoxy, ethoxy, propoxy, isopropoxy, butoxy, isobutoxy, pentoxy, isopentoxy, hexoxy, heptoxy, octyloxy, methylthio, ethylthio, propylthio, isopropylthio, butylthio, isobutylthio, pentylthio, isopentylthio, neopentylthio, hexylthio, heptylthio, octylthio, cyclopentoxy, cyclohexoxy, cycloheptoxy, cyclopentylthio, cyclohexylthio, cycloheptylthio, 2-hydroxyethoxy, 3-hydroxy-propoxy, 4-hydroxy-butoxy, 2-methoxy-ethoxy, 3-ethoxy-propoxy, 4-methoxy-butoxy, benzyloxy, methyl-benzyloxy, isopropyl-benzyloxy, fluoro-benzyloxy, chloro-benzyloxy, dichloro-benzyloxy bromo-benzyloxy, methoxy-benzyloxy, dimethoxybenzyloxy, methylenedioxy-benzyloxy, ethoxybenzyloxy, methylthio-benzyloxy, trifluoromethyl-benzyloxy, nitro-benzyloxy, 2-phenyl-ethoxy, 3-phenylpropoxy, 4-phenyl-butoxy, 2-dimethylamino-ethoxy, 3-diethylamino-propoxy, methoxycarbonyl-methoxy, 2-ethoxycarbonyl-ethoxy, 2-hydroxyethyl-thio, 4-hydroxybutylthio, 2-methoxyethyl-thio, 3-methoxypropyl-thio, 4-methoxybutyl-thio, benzylthio, methylbenzyl-thio, ethylbenzyl-thio, fluorobenzyl-thio, chlorobenzyl-thio, bromobenzyl-thio, dichlorobenzyl-thio, methoxybenzylthio, isopropoxybenzyl-thio, dimethoxybenzyl-thio, methylenedioxybenzyl-thio, nitrobenzyl-thio, trifluoromethylbenzyl-thio, methylthiobenzyl-thio, 2-phenylethyl-thio, 3-phenylpropyl-thio, 4-phenylbutyl-thio, ethoxycarbonylmethyl-thio, 2-diethylaminoethyl-thio, furfuryloxy, furfuryl-thio, naphthylmethyl-thio, naphthylmethoxy, indanyl-thio, indanyloxy, phenylthio, methylphenyl-thio, propylphenyl-thio, hydroxyphenyl-thio, methoxyphenyl-thio, fluorophenyl-thio, chlorophenyl-thio, dichlorophenylthio, bromophenyl-thio, dimethoxyphenyl-thio, methylenedioxyphenyl-thio, methylthiophenyl-thio, amino, methylamino, ethylamino, propylamino, isopropylamino, butylamino, isobutylamino, pentylamino, isopentylamino, neopentylamino, hexylamino, heptylamino, octylamino, cyclohexyl-amino, hydroxycyclohexyl-amino, 2-hydroxyethyl-amino, 3-hydroxypropyl-amino, 4-hydroxybutyl-amino, 5-hydroxypentylamino, 8-hydroxyoctylamino, 1,5-dimethyl-5-hydroxyhexyl-amino, 2-methoxyethyl-amino, 2-(2-hydroxyethoxy)-ethylamino, 3-methoxypropyl-amino, 3-(2-hydroxy-ethoxy)-propylamino, 3-ethoxypropyl-amino, benzylamino, 1-phenylethyl-amino, 2-phenylethyl-amino, 3-phenylpropyl-amino, 4-phenylbutyl-amino, methylbenzyl-amino, methoxybenzyl-amino, dimethoxybenzyl-amino, methylenedioxybenzyl-amino, fluorobenzyl-amino, chlorobenzyl-amino, bromobenzyl-amino, dichlorobenzyl-amino, trifluoromethylbenzylamino, methylthiobenzyl-amino, 2-(dimethoxyphenyl)ethyl-amino, cyclohexylmethyl-amino, furfuryl-amino, pyridylmethyl-amino, phenylamino, methoxyphenyl-amino, ethoxyphenyl-amino, fluorophenyl-amino, chlorophenyl-amino, bromophenyl-amino, dimethoxyphenyl-amino trifluorophenyl-amino, dimethylamino, diethylamino, dipropylamino, diisopropylamino, dibutylamino, dicyclopentylamino, dicyclohexylamino, dicycloheptylamino, N-methyl-ethylamino, N-ethyl-butylamino, N-methyl-cyclohexylamino, N-ethylcyclohexylamino, bis-(2-dimethoxy-ethyl)-amino, N-methylhydroxyethylamino, N-methyl-(2-methoxyethyl)-amino, N-methylphenylamino, N-methyl-trifluorophenylamino, N-methyl-benzylamino, N-methyl-2-(dimethoxyphenyl)-ethylamino, N-methylpyridylmethylamino, pyrrolidino, piperidino, methyl-piperidino, dimethyl-piperidino, ethyl-piperidino, hydroxy-piperidino, tetrahydropyridino, hexamethyleneimino, heptamethyleneimino, tetrahydroquinolino, tetrahydroisoquinolino or furfurylamino.

A preferred subgenus is constituted by those compounds of the formula I wherein $R_1$ is alkyl of 2 to 8 carbon atoms, optionally substituted in the 2- to 8-positions by up to 5 hydroxyls; 2-methoxy-ethyl; 2-amino-ethyl; 2-diethylamino-ethyl; or 2-morpholino-ethyl; methyl; or pyridylmethyl;

$R_2$ is hydrogen; or alkyl of 1 to 3 carbon atoms optionally mono-substituted in the 2- or 3-position by hydroxyl or methoxy; or $R_1$ and $R_2$, together with each other and the nitrogen atoms to which they are attached, are piperidino, optionally mono-substituted by hydroxyl, methoxy, hydroxymethyl, dimethylamino, acetamino, aminocarbonyl or ethoxycarbonyl; morpholino; 1-oxido-thiomorpholino; or imidazolyl;

$R_3$ is morpholino, dimethyl-morpholino, thiomorpholino, 1-oxido-thiomorpholino or 1,1-dioxidothiomorpholino;

$R_4$ is alkoxy of 1 to 8 carbon atoms; phenyl-(alkoxy of 1 to 4 carbon atoms); cyclohexyloxy; alkylthio of 1 to 8 carbon atoms; phenyl-(alkylthio of 1 to 4 carbon atoms); phenylthio; where the phenyl moieties of afore-mentioned benzyloxy, benzylthio or phenylthio groups may be methylenedioxy-substituted, mononitro-substituted or mono- or di-substituted by methyl, hydroxyl, methoxy, methylthio, trifluoromethyl, fluorine, chlorine or bromine; cyclohexylthio; 2-hydroxyethyl-thio; 2-diethylamino-ethyl-thio; ethoxycarbonyl-methylthio; α-methyl-methylthiobenzyl-thio; naphthylmethyl-thio; furfuryl-thio; indanyl; or

$R_6$ is hydrogen; alkyl of 1 to 4 carbon atoms; or alkyl of 2 to 3 carbon atoms substituted in the 2- or 3-position by methoxy; and $R_7$ is hydrogen; alkyl of 1 to 8 carbon atoms, hydroxy-(alkyl of 2 to 8 carbon atoms); alkyl of 2 to 3 carbon atoms mono-substituted in the 2- or 3- position by methoxy, ethoxy or hydroxy-ethoxy; phenyl-(alkyl of 2 carbon atoms), optionally mono- or di-methoxy-substituted on the phenyl moiety; cyclohexyl; hydroxycyclohexyl; cyclohexyl-methyl; 3-phenyl-propyl; 4-phenyl-butyl; furfuryl; pyridylmethyl; phenyl, optionally methylenedioxy-substituted or mono- or di-substituted by methyl, hydroxyl, methoxy, ethoxy, methylthio, trifluoromethyl, fluorine and/or chlorine; or benzyl, optionally methylenedioxy-substituted or mono- or di-substituted by methyl, hydroxyl, methoxy, ethoxy, methylthio, trifluoromethyl, fluorine and/or chlorine on the phenyl moiety; or $R_6$ and $R_7$, together with each other and the nitrogen atom to which they are attached, are pyrrolidino, piperidino, methyl-piperidino, ethyl-piperidino, dimethyl-piperidino, hydroxy-piperidino, hexamethyleneimino, heptamethyleneimino, tetrahydropyridino, tetrahydroquinolino or tetrahydroisoquinolino;

and non-toxic, pharmacologically acceptable acid addition salts thereof.

An especially preferred subgenus is constituted by compounds of formula I wherein $R_1$ is alkyl of 2 to 5 carbon atoms, optionally mono- or di-hydroxy-substituted or mono-methoxy-substituted in the 2- to 5-position;

$R_2$ is hydrogen or 2-hydroxy-ethyl;

$R_3$ is 1-oxido-thiomorpholino;

$R_4$ is alkoxy of 1 to 6 carbon atoms, phenyl(alkoxy of 1 to 3 carbon atoms), alkylthio of 1 to 6 carbon atoms, phenyl-(alkylthio of 1 to 3 carbon atoms), cyclohexylthio or

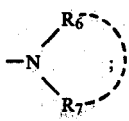

$R_6$ is hydrogen or alkyl of 1 to 4 carbon atoms; and $R_7$ is alkyl of 2 to 5 carbon atoms; mono-hydroxy-substituted alkyl of 2 to 5 carbon atoms; or mono-phenyl-substituted alkyl of 1 to 4 carbon atoms; where the phenyl moiety of aforementioned benzylamino, benzyloxy or benzylthio groups may be mono- or di-substituted by fluorine, chlorine and/or methoxy; or $R_6$ and $R_7$, together with each other and the nitrogen atoms to which they are attached, are pyrrolidino, piperidino or hexamethyleneimino;

and non-toxic, pharmacologically acceptable acid addition salts thereof.

The compounds embraced by formula I may be prepared by the following methods:

Method A

By reacting a trisubstituted pyrimido[5,4-d]pyrimidine or the formula

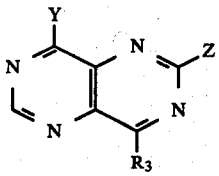

wherein $R_3$ has the same meanings as in formula I;

Y is a nucleophilic leaving group or $R_4$, where $R_4$ has the same meanings as in formula I; and Z is a nucleophilic leaving group;

with an amine of the formula $$H-A \qquad (III)$$

wherein

A is

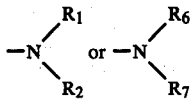

where $R_1$, $R_2$, $R_6$ and $R_7$ have the same meanings as in formula I.

Examples of nucleophilic leaving groups are halogen such as chlorine or bromine, substituted hydroxyl such as phenoxy, or sulfonyl such as methylsulfonyl.

The reaction is advantageously carried out in an inert solvent such as acetone, methyl ethyl ketone, tetrahydrofuran, dioxane, chlorobenzene, dimethylformamide or dimethylsulfoxide, optionally in the presence of an inorganic base such as sodium carbonate or potassium hydroxide, or of a tertiary organic base such as triethylamine or pyridine, where the latter can at the same time also serve as solvents, and optionally in the presence of a reaction accelerator such as a copper salt, a corresponding amine hydrohalide or alkali metal halide, at temperatures between 0° and 150° C., but preferably at temperatures between 20° and 120° C. However, the reaction can also be carried out without a solvent or in an excess of compound of the formula III.

Method B

For the preparation of a compound of the formula I wherein $R_4$ is $-S-R_5$, by reacting a pyrimido[5,4-d]pyrimidine of the formula

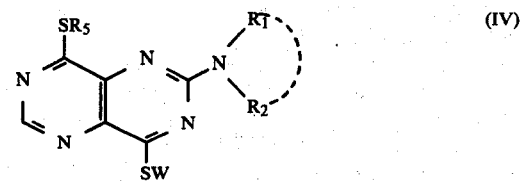

wherein $R_1$, $R_2$ and $R_5$ have the same meanings as in formula I, and

W is lower alkyl such as methyl, ethyl or propyl, or aralkyl such as benzyl, methylbenzyl, chlorobenzyl, nitrobenzyl or naphthylmethyl, with an amine of the formuala $$H-R_3 \qquad (V)$$

wherein $R_3$ has the same meanings as in formula I.

The reaction is advantageously carried out in a solvent such as benzene, tetrahydrofuran, dioxane, dimethylformamide, ethanol or isopropanol, or in an excess of the amine of the formula V, and at elevated temperatures between 60° and 150° C., but preferably at temperatures between 70° and 120° C. However, the reaction can also be carried out without a solvent.

If a compound of the formula I in which $R_3$ is thiomorpholino, optionally substituted by one or two alkyl groups of 1 to 3 carbon atoms each, is obtained, this compound can be converted by means of oxidation into a corresponding thiomorpholino-1-oxide compound; or if a compound of the formula I in which $R_3$ is thiomorpholino or thiomorpholino-1-oxide, optionally substituted by one or two alkyl groups of 1 to 3 carbon atoms each, is thus obtained, this compound can be converted by means of oxidation into a corresponding thiomorpholino-1,1-dioxide compound of the formula I.

The subsequent oxidation is preferably carried out in a solvent such as water, water/pyridine, glacial acetic acid or methanol, and depending upon the oxidizing agent which is used, at temperatures between −80° and +100° C.

To prepare a thiomorpholino-1-oxide of the formula I, the subsequent oxidation is advantageously carried out with one equivalent of the oxidizing agent which is used, for example with hydrogen peroxide in glacial acetic acid at 0° to 20° C., with a peracid such as peracetic acid, m-chloroperbenzoic acid or peroxytrifluoroacetic acid at 0° to 50° C., with potassium permanganate in dilute hydrochloric acid at 0° C., with sodium metaperiodate in aqueous methanol or ethanol at 15° to 25° C., with tert. butyl hypochlorite in methanol at −80° to −30° C., with iodobenzene dichloride in aqueous pyridine at 0° to 50° C., with nitric acid in glacial acetic acid or acetone at 0° to 20° C.

To prepare a thiomorpholino-1,1-dioxide of the formula I, the subsequent oxidation is advantageously carried out with two equivalents of the particular oxidizing agent, starting from a thiomorpholino compound of the formula I, or with one equivalent, starting from a thiomorpholino-1-oxide compound of the formula I, in a way similar to that described above. However, the reaction is carried out at a reaction temperature 10° to 50° C. higher.

The compounds of the formula I are basic and therefore form addition salts with inorganic or organic acids. Examples of non-toxic, pharmacologically acceptable acid addition salts are those formed with hydrochloric acid, hydrobromic acid, sulfuric acid phosphoric acid, methanesulfonic acid, p-toluenesulfonic acid, acetic acid, lactic acid, citric acid, tartaric acid, succinic acid, maleic acid, fumaric acid, salicylic acid or the like.

The starting compounds of the formula II through V are either described in the literature or are obtainable by methods described in the literature. Thus, for example, the starting compounds of the formulas II and IV are obtained by stepwise replacement of the chlorine atoms of 2,4,8-trichloropyrimido[5,4-d]pyrimidine (see German Pat. No. 1,116,676).

The following examples illustrate the present invention and will enable others skilled in the art to understand it more completely. It should be understood, however, that the invention is not limited solely to the particular examples given below.

The melting points given in these examples are uncorrected.

PREPARATION OF STARTING COMPOUNDS

EXAMPLE A 2,8-Dichloro-4-morpholino-pyrimido[5,4-d]pyrimidine 118 gm (0.5 mol) of 2,4,8-trichloro-pyrimido[5,4-d]-pyrimidine were suspended in 1.2 liters of acetone, and a solution of 44 ml (0.5 mol) of morpholine and 70 ml (0.5 mol) of triethylamine in 100 ml of acetone was added slowly to the suspension at room temperature, while stirring. After stirring the mixture for about half an hour more, 1.3 liters of water were added to the reaction mixture, whereby the triethylamine hydrochloride dissolved and further reaction product precipitated. After standing for a little while, the precipitate was suction-filtered off, washed well first with water and then with some methanol, and dried at 60° C. Yield: 132 gm (92% of theory), melting point 179°–181° C.

Melting point: 183°–185° C. (from ethanol).

The reaction can also be carried out in completely analogous manner using an aqueous potassium carbonate solution instead of triethylamine.

The following compounds were prepared analogously:

2,8-Dichloro-4-(2-methyl-morpholino)-pyrimido[5,4-d]-pyrimidine. Melting point: 129°–131° C.;
2,8-Dichloro-4-(2,6-dimethylmorpholino)-pyrimido[5,4-d]-pyrimidine. Melting point: 181°–183° C.;
2,8-Dichloro-4-thiomorpholino-pyrimido[5,4-d]-pyrimidine. Melting point: 154°–157° C.;
2,8-Dichloro-4-(1-oxido-thiomorpholino)-pyrimido[5,4-d]-pyrimidine. Melting point: 195°–198° C. (dioxane);
2,8-Dichloro-4-(1,1-dioxido-thiomorpholino)-pyrimido[5,4-d]-pyrimidine. Melting point: 270°–273° C. (decomposition, dioxane).

EXAMPLE B

8-Benzylthio-2-chloro-4-morpholino-pyrimido[5,4-d]pyrimidine

A solution of 23 gm (0.52 mol) of sodium methylate in 150 ml of methanol and 59 ml (0.5 mol) of benzylmercaptan was slowly added, while stirring, at room temperature to a suspension of 143 gm (0.5 mol) of 2,8-dichloro-4-morpholinopyrimido[5,4-d]pyrimidine in 2 liters of acetone. The mixture was stirred for about one hour more, and about 2 liters of water were then added to the reaction mixture, whereby the precipitated sodium chloride dissolved and further reaction product precipitated. After standing for a little while, the precipitate was suction-filtered off, washed first with about 1 liter of water and then with about 500 ml of methanol, and dried at 60° C.

Yield: 182 gm (97% of theory), melting point 157°–159° C.

Melting point: 159°–161° C. (from isopropanol).

The reaction can also be carried out in completely analogous manner, using 2N sodium hydroxide instead of a sodium methylate solution.

EXAMPLE C 8-(N-Benzyl-methylamino)-2-chloro-4-(1-oxido-thiomorpholino)pyrimido[5,4-d]pyrimidine A solution of 12.2 gm (0.1 mol) of N-benzyl-methylamine in 50 ml of dioxane was slowly poured, while stirring, into a suspension of 15.9 gm (0.05 mol) of 2,8-dichloro-4-(1-oxido-thiomorpholino)-pyrimido[5,4-d]-pyrimidine in about 250 ml of dioxane, and the resulting mixture was heated at 30°–40° C. for about 30 minutes. The reaction mixture was taken up in about 1 liter of water, whereby the reaction product was precipitated as a slightly yellow precipitate. After standing for a little while, the precipitate was filtered off, washed with water and dried at about 60° C.

Yield: 18.6 gm (92% of theory).

After recrystallization from ethanol, the 8-(N-benzyl-methylamino)-2-chloro-4-(1-oxido-thiomorpholino)-pyrimido[5,4-d]-pyrimidine melted at 158°–160° C.

EXAMPLE D

8-Benzyloxy-2-chloro-4-(1-oxido-thiomorpholino)-pyrimido[5,4-d]-pyrimidine

An alcoholate solution, prepared from 22 gm (0.2 mol) of benzyl alcohol in 100 ml of absolute benzene with 1.6 gm (0.07 mol) of sodium, was added to a solution of 15.9 gm (0.05 mol) of 2,8-dichloro-4-(1-oxido-thiomorpholino)pyrimido[5,4-d]-pyrimidine in 400 ml of dioxane at about 30° C., and the mixture thus obtained was stirred at room temperature for about two hours. The reaction mixture was then evaporated in vacuo, and the residue was admixed with about 500 ml of water. The precipitate which solidified after standing for a short time, was filtered off, washed with water and dried at about 70° C.

Yield: 16 gm (82% of theory).

After recrystallization from dioxane, the 8-benzyloxy-2-chloro-4-(1-oxido-thiomorpholino)-pyrimido[5,4-d]pyrimidine melted at 227°–229° C.

All the starting compounds used in the following examples were prepared analogous to Examples B, C or D.

PREPARATION OF THE END PRODUCTS OF THE FORMULA I

EXAMPLE 1

8-Benzylthio-2-(2-hydroxyethyl-amino)-4-(1-oxido-thiomorpholino)-pyrimido[5,4-d]pyrimidine 20.3 gm (0.05 mol) of 8-benzylthio-2-chloro-4-(1-oxido-thiomorpholino)-pyrimido[5,4-d]pyrimidine (melting point: 188°-190° C.) were refluxed for about 45 minutes with 8 gm (0.13 mol) of 2-hydroxyethyl-amine in 400 ml of dioxane. Most of the solvent was distilled off in vacuo, and the residue was taken up in about 500 ml of water. The reaction product, which precipitated after standing for a little while, was filtered off, washed with water and dried at about 70° C.

Yield: 20.8 gm (97% of theory).

After recrystallization from ethanol/dioxane, the 8-benzylthio-2-(2-hydroxyethyl-amino)-4-(1-oxido-thiomorpholino)-pyrimido[5,4-d]pyrimidine melted at 215°-217° C.

$C_{19}H_{22}N_6O_2S_2$ (430.6):

Calculated: C—52.99%; H—5.16%; N—19.52%; S—14.89%.

Found: C—53.00%; H—5.23%; N—19.56%; S—14.70%.

The same compound was also obtained by reacting 4,8-bis-(benzylthio)-2-(2-hydroxyethyl-amino)-pyrimido[5,4-d]pyrimidine (melting point: 154°-155° C.) with thiomorpholino-1-oxide at 80° to 100° C. in the presence of thiomorpholine-1-oxide hydrochloride, or by oxidation of 8-benzylthio-2-(2-hydroxyethyl-amino)-4-thiomorpholinopyrimido[5,4-d]pyrimidine (melting point: 175°-177° C.)

(a) with sodium metaperiodate in methanol under reflux,
(b) with hydrogen peroxide in glacial acetic acid at about 30° C., or
(c) with potassium permanganate in 1N hydrochloric acid at 30° C.

EXAMPLE 2

8-(N-Benzyl-methylamino)-2-(2-hydroxyethyl-amino)-4-(1-oxido-thiomorpholino)-pyrimido[5,4-d]pyrimidine 8.1 gm (0.02 mol) of 8-(N-benzyl-methylamino)-2-chloro-4-(1-oxido-thiomorpholino)-pyrimido[5,4-d]pyrimidine (melting point: 158°-160° C.) were heated at about 90° C. for one hour with 12.2 gm (0.2 mol) of 2-hydroxyethyl-amine. The mixture thus obtained was taken up in about 250 ml of water, whereby the reaction product separated out as a precipitate which soon solidified. It was filtered off, washed with water and dried at about 60° C. Yield: 8.2 gm (96% of theory).

After recrystallization from ethanol, the 8-(N-benzylmethylamino)-2-(2-hydroxyethyl-amino)-4-(1-oxidothiomorpholino)-pyrimido[5,4-d]pyrimidine melted at 181°-182° C.

$C_{20}H_{25}N_7O_2S$ (427.5):

Calculated: C—56.19%; H—5.89%; N—22.48%; S—7.50%.

Found: C—56.30%; H—5.78%; N—22.45%; S—7.32%.

EXAMPLE 3

2-Diethanolamino-4-(1-oxido-thiomorpholino)-8-piperidinopyrimido[5,4-d]pyrimidine 11.0 gm (0.03 mol) of 2-chloro-4-(1-oxido-thiomorpholino)-8-piperidino-pyrimido[5,4-d]pyrimidine (melting point: 203°-204° C.) were heated at 120° C. for about 30 minutes with 32 gm (0.3 mol) of diethanolamine, and the mixture thus obtained was subsequently taken up in about 300 ml of water. The reaction product which precipitated in crystalline form after a short time was filtered off, washed with water and dried.

Yield: 12.4 gm (95% of theory).

After recrystallization from ethanol, the 2-diethanolamino-4-(1-oxido-thiomorpholino)-8-piperidinopyrimido[5,4-d]pyrimidine melted at 115°-118° C.

$C_{19}H_{29}N_7O_3S$ (435.6):

Calculated: C—52.39%; H—6.71%; N—22.51%; S—7.36%.

Found: C—53.03%; H—6.70%; N—22.63%; S—7.09%.

EXAMPLE 4

8-Benzyloxy-2-diethanolamino-4-(1-oxido-thiomorpholino)pyrimido[5,4-d]pyrimidine 7.8 gm (0.02 mol) of 8-benzyloxy-2-chloro-4-(1-oxidothiomorpholino)-pyrimido[5,4-d]pyrimidine (melting point: 227°-229° C.) were heated at 100° C. for about one hour with 8.4 gm (0.08 mol) of diethanolamine in 100 ml of dioxane (or without a solvent). The solvent was distilled off in vacuo, and the residue was taken up in about 300 ml of water. The reaction product which solidified after standing for a little while was filtered off, washed with water and dried at about 60° C.

Yield: 8.4 gm (92% of theory).

After recrystallization from ethanol, the 8-benzyloxy2-diethanolamino-4-(1-oxido-thiomorpholino)-pyrimido[5,4-d]-pyrimidine melted at 175°-177° C.

$C_{21}H_{26}N_6O_4S$ (458.6):

Calculated: C—55.01%; H—5.72%; N—18.33%; S—6.99%.

Found: C—55.30%; H—5.80%; N—18.55%; S—6.84%.

EXAMPLE 5

2-(2-Hydroxyethyl-amino)-8-methylthio-4-(1-oxidothiomorpholino)-pyrimido[5,4-d]pyrimidine This compound was prepared analogous to Example 1 from 2-chloro-8-methylthio-4-(1-oxido-thiomorpholino)pyrimido[5,4d]pyrimidine (melting point: 260°-262° C.) and 2-hydroxyethyl-amine.

Melting point: 168°-170° C. (methanol).

EXAMPLE 6

2-Diethanolamino-8-methylthio-4-(1-oxido-thiomorpholino)pyrimido[5,4-d]pyrimidine This compound was prepared analogous to Example 3 from 2-chloro-8-methylthio-4-(1-oxido-thiomorpholino)pyrimido[5,4-d]pyrimidine and diethanolamine.

Melting point: 228°-230° C. (dimethylformamide).

EXAMPLE 7

2-(2-Hydroxyethyl-amino)-4-(1-oxido-thiomorpholino)-8-propylthio-pyrimido[5,4-d]pyrimidine This compound was prepared analogous to Example 1 from 2-chloro-4-(1-oxido-thiomorpholino)-8-propylthiopyrimido[5,4-d]pyrimidine (melting point: 209°-210° C.) and 2-hydroxyethyl-amine.

Melting point: 170°-172° C. (ethanol).

EXAMPLE 8

2-(2-Hydroxyethyl-amino)-8-isopentylthio-4-(1-oxido-thiomorpholino)-pyrimido[5,4-d]pyrimidine This compound was prepared analogous to Example 1 from 2-chloro-8-isopentylthio-4-(1-oxido-thiomorpholino)pyrimido[5,4-d]pyrimidine (melting point: 175°-177° C.) and 2-hydroxyethyl-amine.

Melting point: 200°–202° C. (ethanol).

EXAMPLE 9

2-(2-Hydroxyethyl-amino)-8-octylthio-4-(1-oxidothiomorpholino)-pyrimido[5,4-d]pyrimidine This compound was prepared analogous to Example 1 from 2-chloro-8-octylthio-4-(1-oxido-thiomorpholino)pyrimido[5,4-d]pyrimidine (melting point: 106°–108° C.) and 2-hydroxyethyl-amine.
Melting point: 158°–160° C. (ethanol).

EXAMPLE 10

8-Cyclohexylthio-2-(2-hydroxyethyl-amino)-4-(1-oxidothiomorpholino)-pyrimido[5,4-d]pyrimidine This compound was prepared analogous to Example 1 from 2-chloro-8-cyclohexylthio-4-(1-oxido-thiomorpholino)pyrimido[5,4-d]pyrimidine (melting point: 225°–227° C.) and 2-hydroxyethyl-amine.
Melting point: 204°–206° C. (ethanol).

EXAMPLE 11

8-Benzylthio-2-(2-hydroxyethyl-amino)-4-morpholinopyrimido[5,4-d]pyrimidine

This compound was prepared analogous to Example 1 from 8-benzylthio-2-chloro-4-morpholinopyrimido[5,4-d]pyrimidine (melting point: 159°–161° C.) and 2-hydroxyethylamine by heating in dimethylsulfoxide at 50° C.
Melting point: 151°–153° C. (ethyl acetate).

The same substance was also obtained in analogous manner by heating 8-benzylthio-4-morpholino-2-phenoxypyrimido[5,4-d]pyrimidine (melting point: 159°–161° C.) at 90° C. with 2-hydroxyethyl-amine.

EXAMPLE 12

8-Benzylthio-2-(2-hydroxyethyl-amino)-4-thiomorpholinopyrimido[5,4-d]pyrimidine

This compound was prepared analogous to Example 1 from 8-benzylthio-2-chloro-4-thiomorpholinopyrimido[5,4-d]pyrimidine (melting point: 175°–177° C.) and 2-hydroxyethyl-amine.
Melting point: 155°–157° C. (ethanol/dioxane).

EXAMPLE 13

8-Benzylthio-4-(1,1-dioxido-thiomorpholino)-2-(2-hydroxyethylamino)-pyrimido[5,4-d]pyrimidine This compound was prepared analogous to Example 1 from 8-benzylthio-2-chloro-4-(1,1-dioxido-thiomorpholino)pyrimido[5,4-d]pyrimidine (melting point: 230°–233° C.) and 2-hydroxyethyl-amine.
Melting point: 193°–195° C. (ethyl acetate).

EXAMPLE 14

8-Benzylthio-2-diethanolamino-4-(1-oxido-thiomorpholino)pyrimido[5,4-d]pyrimidine This compound was prepared analogous to Example 1 from 8-benzylthio-2-chloro-4-(1-oxido-thiomorpholino)pyrimido[5,4-d]pyrimidine (melting point: 188°–190° C.) and diethanolamine by refluxing for three hours.
Melting point: 186°–188° C. (ethanol).

EXAMPLE 15

8-Benzylthio-2-[N-(2-hydroxy-ethyl)-methylamino]-4-(1-oxido-thiomorpholino)-pyrimido[5,4-d]pyrimidine This compound was prepared analogous to Example 1 from 8-benzylthio-2-chloro-4-(1-oxido-thiomorpholino)-pyrimido[5,4-d]pyrimidine and N-methylethanolamine.
Melting point: 177°–179° C. (ethanol).

EXAMPLE 16

8-Benzylthio-2-[N-(2-hydroxy-ethyl)-2-methoxyethyl-amino]4-(1-oxido-thiomorpholino)-pyrimido[5,4-d]pyrimidine This compound was prepared analogous to Example 1 from 8-benzylthio-2-chloro-4-(1-oxido-thiomorpholino)pyrimido[5,4-d]pyrimidine and N-methoxyethyl-ethanolamine.
Melting point: 136°–138° C. (ethyl acetate).

EXAMPLE 17

8-Benzylthio-2-(3-hydroxypropyl-amino)-4-(1-oxidothiomorpholino)-pyrimido[5,4-d]pyrimidine This compound was prepared analogous to Example 1 from 8-benzylthio-2-chloro-4-(1-oxido-thiomorpholino)-pyrimido[5,4-d]pyrimidine and 3-amino-1-propanol.
Melting point: 148°–150° C. (ethanol).

EXAMPLE 18

8-Benzylthio-2-(2-hydroxypropyl-amino)-4-(1-oxidothiomorpholino)-pyrimido[5,4-d]pyrimidine This compound was prepared analogous to Example 1 from 8-benzylthio-2-chloro-4-(1-oxido-thiomorpholino)pyrimido[5,4-d]pyrimidine and 1-amino-2-propanol.
Melting point: 175°–177° C.

EXAMPLE 19

8-Benzylthio-2-(2,3-dihydroxypropyl-amino)-4-(1-oxidothiomorpholino)-pyrimido[5,4-d]pyrimidine This compound was prepared analogous to Example 1 from 8-benzylthio-2-chloro-4-(1-oxido-thiomorpholino)pyrimido[5,4-d]pyrimidine and 1-amino-2,3-propandiol.
Melting point: 167°–169° C. (ethanol).

EXAMPLE 20

8-Benzylthio-2-(5-hydroxypentyl-amino)-4-(1-oxidothiomorpholino)-pyrimido[5,4-d]pyrimidine This compound was prepared analogous to Example 1 from 8-benzylthio-2-chloro-4-(1-oxido-thiomorpholino)pyrimido[5,4-d]pyrimidine and 5-amino-1-pentanol.
Melting point: 158°–159° C. (ethanol).

EXAMPLE 21

8-Benzylthio-2-(6-hydroxyhexyl-amino)-4-(1-oxidothiomorpholino)-pyrimido[5,4-d]pyrimidine This compound was prepared analogous to Example 1 from 8-benzylthio-2-chloro-4-(1-oxido-thiomorpholino)pyrimido[5,4-d]pyrimidine and 6-amino-1-hexanol.
Melting point: 125°–127° C. (ethanol).

EXAMPLE 22

8-Benzylthio-2-(N-methyl-D-glucamino)-4-(1-oxidothiomorpholino)-pyrimido[5,4-d]pyrimidine This compound was prepared analogous to Example 1 from 8-benzylthio-2-chloro-4-(1-oxido-thiomorpholino)pyrimido[5,4-d]pyrimidine and N-methyl-D-glucamine.

Melting point: 203°–205° C. (dioxane).

EXAMPLE 23

8-Benzylthio-2-methylamino-4-(1-oxido-thiomorpholino)pyrimido[5,4-d]pyrimidine

This compound was prepared analogous to Example 1 from 8-benzylthio-2-chloro-4-(1-oxido-thiomorpholino)pyrimido[5,4-d]pyrimidine and methylamine in dioxane at about 100° C. under pressure.

Melting point: 190°–192° C. (ethanol/dioxane).

EXAMPLE 24

8-Benzylthio-4-(1-oxido-thiomorpholino)-2-propylaminopyrimido[5,4-d]pyrimidine

This comppund was prepared analogous to Example 23 from 8-benzylthio-2-chloro-4-(1-oxido-thiomorpholino)pyrimido[5,4-d]pyrimidine and propylamine.

Melting point: 181°–182° C. (ethanol/dioxane).

EXAMPLE 25

8-Benzylthio-2-isopentylamino-4-(1-oxido-thiomorpholino)pyrimido[5,4-d]pyrimidine This compound was prepared analogous to Example 1 from 8-benzylthio-2-chloro-4-(1-oxido-thiomorpholino)pyrimido[5,4-d]pyrimidine and 3-methylbutylamine.

Melting point: 195°–197° C. (ethanol/dioxane).

EXAMPLE 26

2-(2-Aminoethyl-amino)-8-benzylthio-4-(1-oxidothiomorpholino)-pyrimido[5,4-d]pyrimidine This compound was prepared analogous to Example 1 from 8-benzylthio-2-chloro-4-(1-oxido-thiomorpholino)pyrimido[5,4-d]pyrimidine and ethylenediamine.

Melting point: 174°–176° C. (ethanol).

EXAMPLE 27

8-Benzylthio-2-(2-diethylaminoethyl-amino)-4-(1-oxidothiomorpholino)-pyrimido[5,4-d]pyrimidine This compound was prepared analogous to Example 1 from 8-benzylthio-2-chloro-4-(1-oxido-thiomorpholino)-pyrimido[5,4-d]pyrimidine and 2-diethylaminoethyl-amine.

Melting point: 112°–115° C. (ethanol).

EXAMPLE 28

8-Benzylthio-2-(2-morpholinoethyl-amino)-4-(1-oxido-thiomorpholino)-pyrimido[5,4-d]pyrimidine This compound was prepared analogous to Example 1 from 8-benzylthio-2-chloro-4-(1-oxido-thiomorpholino)pyrimido[5,4-d]pyrimidine and 2-morpholinoethyl-amine.

Melting point: 187°–190° C.

EXAMPLE 29

8-Benzylthio-4-(1-oxido-thiomorpholino)-2-(3-picolylamino)pyrimido[5,4-d]pyrimidine This compound was prepared analogous to Example 1 from 8-benzylthio-2-chloro-4-(1-oxido-thiomorpholino)pyrimido[5,4-d]pyrimidine and 3-picolylamine.

Melting point: 145°–148° C. (ethanol).

EXAMPLE 30

8-Benzylthio-2-(N-methyl-3-picolylamino)-4-(1-oxido-thiomorpholino)-pyrimido[5,4-d]pyrimidine This compound was prepared analogous to Example 1 from 8-benzylthio-2-chloro-4-(1-oxido-thiomorpholino)-pyrimido[5,4-d]pyrimidine and N-methyl-3-picolylamine.

Melting point: 186°–188° C. (ethanol).

EXAMPLE 31

8-Benzylthio-2-(3-hydroxy-piperidino)-4-(1-oxidothiomorpholino)-pyrimido[5,4-d]pyrimidine This compound was prepared analogous to Example 1 from 8-benzylthio-2-chloro-4-(1-oxido-thiomorpholino)pyrimido[5,4-d]pyrimidine and 3-hydroxypiperidine.

Melting point: 239°–241° C. (ethanol).

EXAMPLE 32

8-Benzylthio-2-(4-hydroxy-piperidino)-4-(1-oxidothiomorpholino)-pyrimido[5,4-d]pyrimidine This compound was prepared analogous to Example 1 from 8-benzylthio-2-chloro-4-(1-oxido-thiomorpholino)pyrimido[5,4-d]pyrimidine and 4-hydroxypiperidine.

Melting point: 247°–249° C. (ethanol).

EXAMPLE 33

8-Benzylthio-2-(4-methoxy-piperidino)-4-(1-oxidothiomorpholino) pyrimido[5,4-d]pyrimidine This compound was prepared analogous to Example 1 from 8-benzylthio-2-chloro-4-(1-oxido-thiomorpholino)pyrimido[5,4-d]pyrimidine and 4-methoxypiperidine.

Melting point: 196°–199° C. (ethanol).

EXAMPLE 34

8-Benzylthio-2-(2-hydroxymethyl-piperidino)-4-(1-oxidothiomorpholino)-pyrimido[5,4-d]pyrimidine This compound was prepared analogous to Example 1 from 8-benzylthio-2-chloro-4-(1-oxido-thiomorpholino)pyrimido[5,4-d]pyrimidine and 2-hydroxymethyl-piperidine.

Melting point: 190°–192° C. (ethanol).

EXAMPLE 35

8-Benzylthio-2-(3-hydroxymethyl-piperidino)-4-(1-oxidothiomorpholino)-pyrimido[5,4-d]pyrimidine This compound was prepared analogous to Example 1 from 8-benzylthio-2-chloro-4-(1-oxido-thiomorpholino)pyrimido[5,4-d]pyrimidine and 3-hydroxymethyl-piperidine.

Melting point: 222°–223° C. (dioxane).

EXAMPLE 36

8-Benzylthio-2-(4-methylamino-piperidino)-4-(1-oxido-thiomorpholino)-pyrimido[5,4-d]pyrimidine This compound was prepared analogous to Example 1 from 8-benzylthio-2-chloro-4-(1-oxido-thiomorpholino)pyrimido[5,4-d]pyrimidine and 4-dimethylamino-piperidine.

Melting point: 202°–204° C. (ethanol/dioxane).

EXAMPLE 37

2-(4-Acetylamino-piperidino)-8-benzylthio-4-(1-oxido-thiomorpholino)-pyrimido[5,4-d]pyrimidine This compound was prepared analogous to Example 1 from 8-benzylthio-2-chloro-4-(1-oxido-thiomorpholino)pyrimido[5,4-d]pyrimidine and 4-acetylamino-piperidine.

Melting point: 295°–297° C.

EXAMPLE 38

8-Benzylthio-2-(4-carbamoyl-piperidino)-4-(1-oxidothiomorpholino)-pyrimido[5,4-d]pyrimidine This compound was prepared analogous to Example 1 from 8-benzylthio-2-chloro-4-(1-oxido-thiomorpholino)pyrimido[5,4-d]pyrimidine and piperidino-4-carboxylic acid amide.

Melting point: 270°–273° C.

EXAMPLE 39

2-(4-Ethoxycarbonyl-piperidino)-8-benzylthio-4-(1-oxidothiomorpholino)-pyrimido[5,4-d]pyrimidine This compound was prepared analogous to Example 1 from 8-benzylthio-2-chloro-4-(1-oxido-thiomorhpolino)pyrimido[5,4-d]pyrimidine and ethyl piperidino-4-carboxylate.

Melting point: 192°–194° C. (ethanol).

EXAMPLE 40

2-(3-Ethoxycarbonyl-piperidino)-8-benzylthio-4-(1-oxidothiomorpholino)-pyrimido[5,4-d]pyrimidine This compound was prepared analogous to Example 1 from 8-benzylthio-2-chloro-4-(1-oxido-thiomorpholino)pyrimido[5,4-d]pyrimidine and ethyl piperidino-3-carboxylate.

Melting point: 167°–170° C. (ethanol).

EXAMPLE 41

8-Benzylthio-2-morpholino-4-(1-oxido-thiomorpholino)pyrimido[5,4-d]pyrimidine

This compound was prepared analogous to Example 1 from 8-benzylthio-2-chloro-4-(1-oxido-thiomorpholino)pyrimido[5,4-d]pyrimidine and morpholine.

Melting point: 239°–240° C. (ethanol).

EXAMPLE 42

8-Benzylthio-4-morpholino-2-(1-oxido-thiomorpholino)pyrimido[5,4-d]pyrimidine

This compound was prepared analogous to Example 1 from 8-benzylthio-2-chloro-4-morpholino-pyrimido[5,4-d]pyrimidine melting point: 159°–161° C.) and thiomorpholine-1-oxide.

Melting point: 245°–247° C.

EXAMPLE 43

8-Benzylthio-2-(1-oxido-thiomorpholino)-4-thiomorpholinopyrimido[5,4-d]pyrimidine This compound was prepared analogous to Example 1 from 8-benzylthio-2-chloro-4-thiomorpholinopyrimido[5,4-d]pyrimidine (melting point: 175°–177° C.) and thiomorpholine1-oxide.

Melting point: 204°–205° C.

EXAMPLE 44

8-Benzylthio-2,4-bis-(1-oxido-thiomorpholino)-pyrimido[5,4-d]pyrimidine

This compound was prepared analogous to Example 1 from 8-benzylthio-2-chloro-4-(1-oxido-thiomorpholino)pyrimido[5,4-d]pyrimidine (melting point: 188°–190° C.) and thiomorpholine-1-oxide by refluxing for three hours in dioxane.

Melting point: 208°–211° C.

EXAMPLE 45

8-Benzylthio-2-imidazolyl-4-(1-oxido-thiomorpholino)-pyrimido[5,4-d]pyrimidine

This compound was prepared analogous to Example 1 from 8-benzylthio-2-chloro-4-(1-oxido-thiomorpholino)-pyrimido[5,4-d]pyrimidine and imidazole by refluxing for six hours in dioxane.

Melting point: 260°–262° C.

EXAMPLE 46

2-(2-Hydroxyethylamino)-4-(1-oxido-thiomorpholino)-8-phenethylthio-pyrimido[5,4-d]pyrimidine This compound was prepared analogous to Example 1 from 2-chloro-4-(1-oxido-thiomorpholino)-8-phenethylthiopyrimido[5,4-d]pyrimidine (melting point: 248°–250° C.) and 2-hydroxyethyl-amine.

Melting point: 181°–184° C. (ethanol).

EXAMPLE 47

2-Diethanolamino-4-(1-oxido-thiomorpholino)-8-phenethylthiopyrimido[5,4-d]pyrimidine This compound was prepared analogous to Example 1 from 2-chloro-4-(1-oxido-thiomorpholino)-8-phenethylthiopyrimido[5,4-d]pyrimidine and diethanolamine.

Melting point: 178°–179° C. (ethanol).

EXAMPLE 48

2-(2-Hydroxyethyl-amino)-4-(1-oxido-thiomorpholino)-8-(3-phenylpropyl-thio)-pyrimido[5,4-d]pyrimidine This compound was prepared analogous to Example 1 from 2-chloro-4-(1-oxido-thiomorpholino)-8-(3-phenylpropylthio)-pyrimido[5,4-d]pyrimidine (melting point: 172°–174° C.) and 2-hydroxyethyl-amine.

Melting point: 180°–182° C. (ethanol).

EXAMPLE 49

8-Furfurylthio-2-(2-hydroxyethyl-amino)-4-(1-oxidothiomorpholino)-pyrimido[5,4-d]pyrimidine This compound was prepared analogous to Example 1 from 2-chloro-8-furfurylthio-4-(1-oxido-thiomorpholino)pyrimido[5,4-d]pyrimidine (melting point: 173°–175° C.) and 2-hydroxyethyl-amine.

Melting point: 182°–184° C. (ethanol).

EXAMPLE 50

2-(2-Hydroxyethyl-amino)-8-(2-hydroxyethyl-thio)-4-(1-oxido-thiomorpholino)-pyrimido[5,4-d]pyrimidine This compound was prepared analogous to Example 1 from 2-chloro-8-(2-hydroxyethyl-thio)-4-(1-oxido-thiomorpholino)-pyrimido[5,4-d]pyrimidine (melting point: 228°–230° C., decomposition) and 2-hydroxyethyl-amine.

Melting point: 200°–203° C. (ethanol/ethyl acetate).

EXAMPLE 51

2-Diethanolamino-8-(2-hydroxyethyl-thio)-4-(1-oxido-thiomorpholino)-pyrimido[5,4-d]pyrimidine This compound was prepared analogous to Example 1 from 2-chloro-8-(2-hydroxyethyl-thio)-4-(1-oxidothiomorpholino)-pyrimido[5,4-d]pyrimidine and diethanolamine.

Melting point: 196°–199° C. (ethanol).

EXAMPLE 52

8-Ethoxycarbonylmethylthio-2-(2-hydroxyethyl-amino)-4-1-oxido-thiomorpholino)-pyrimido[5,4-d]pyrimidine This compound was prepared analogous to Example 1 from 8-ethoxycarbonylmethylthio-2-chloro-4-(1-oxido-thiomorpholino)-pyrimido[5,4-d]pyrimidine (melting point: 174°–175° C.) and 2-hydroxyethyl-amine.

Melting point: 172°–174° C. (methanol).

EXAMPLE 53

8-(2-Diethylaminoethyl-thio)-2-(2-hydroxypropyl-amino)4-(1-oxido-thiomorpholino)-pyrimido[5,4-d]pyrimidine This compound was prepared analogous to Example 1 from 2-chloro-8-(2-diethylaminoethyl-thio)-4-(1-oxidothiomorpholino)-pyrimido[5,4-d]pyrimidine (melting point: 146°–148° C.) and 2-hydroxypropyl-amine. Resin.

EXAMPLE 54

2-(2-Hydroxyethyl-amino)-8-(2-indanyl-thio)-4-(1-oxidothiomorpholino)-pyrimido[5,4-d]pyrimidine This compound was prepared analogous to Example 1 from 2-chloro-8-(2-indanyl-thio)-4-(1-oxido-thiomorpholino)pyrimido[5,4-d]pyrimidine (melting point: 268°–270° C.) and 2-hydroxyethyl-amine.

Melting point: 228°–230° C. (dimethylformamide).

EXAMPLE 55

2-(2-Hydroxyethyl-amino)-8-(1-naphthylmethyl-thio)-4-(1-oxidothiomorpholino)-pyrimido[5,4-d]pyrimidine This compound was prepared analogous to Example 1 from 2-chloro-8-(1-naphthylmethyl thio)-4-(1-oxidothiomorpholino)-pyrimido[5,4-d]pyrimidine (melting point: 212°–215° C.) and 2-hydroxyethyl-amine.

Melting point: 210°–211° C. (dimethylformamide).

EXAMPLE 56

2-(2-Hydroxyethyl-amino)-4-(1-oxido-thiomorpholino)-8-phenylthio-pyrimido[5,4-d]pyrimidine This compound was prepared analogous to Example 1 from 2-chloro-4-(1-oxido-thiomorpholino)-8-phenylthiopyrimido[5,4-d]pyrimidine (melting point: 253°–255° C.) and 2-hydroxyethyl-amine.

Melting point: 242°–245° C.

EXAMPLE 57

2-(2-Hydroxyethyl-amino)-4-(1-oxido-thiomorpholino)-8-(4-tolyl-thio)-pyrimido[5,4-d]pyrimidine This compound was prepared analogous to Example 1 from 2-chloro-4-(1-oxido-thiomorpholino)-8-(4-tolyl-thio)pyrimido[5,4-d]pyrimidine (melting point: 261°–263° C.) and 2-hydroxyethyl-amine.

Melting point: 245°–247° C. (ethanol/ethyl acetate).

EXAMPLE 58

2-(2-Hydroxyethyl-amino)-8-(4-methoxyphenyl-thio)-4-1-oxido-thiomorpholino)-pyrimido[5,4-d]pyrimidine This compound was prepared analogous to Example 1 from 2-chloro-8-(4-methoxyphenyl-thio)-4-(1-oxido-thiomorpholino)-pyrimido[5,4-d]pyrimidine (melting point: 239°–241° C. and 2-hydroxyethyl-amine.

Melting point: 221°–223° C. (methanol/dioxane).

EXAMPLE 59

2-Diethanolamino-8-(4-hydroxyphenyl-thio)-4-(1-oxidothiomorpholino)-pyrimido[5,4-d]pyrimidine This compound was prepared analogous to Example 1 from 2-chloro-8-(4-hydroxyphenyl-thio)-4-(1-oxido-thiomorpholino)-pyrimido[ 5,4 -d ](melting point: >280° C.) and diethanolamine.

Melting point: 223°–225° C. (ethanol).

EXAMPLE 60

2-Diethanolamino-8-(4-fluorophenyl-thio)-4-(1-oxido-thiomorpholino)-pyrimido[5,4-d]pyrimidine This compound was prepared analogous to Example 1 from 2-chloro-8-(4-fluoropehnyl-thio)-4-(1-oxidothiomorpholino)-pyrimido[5,4-d]pyrimidine (melting point: 243°–245° C.) and diethanolamine.

Melting point: 210°–212° C. (ethyl acetate/methanol).

EXAMPLE 61

8-(4-Chlorophenyl-thio)-2-(2-hydroxyethyl-amino)-4-(1-oxido-thiomorpholino)-pyrimido[5,4-d]pyrimidine This compound was prepared analogous to Example 1 from 2-chloro-8-(4-chlorophenyl-thio)-4-(1-oxidothiomorpholino)-pyrimido[5,4-d]pyrimidine (melting point: 267°–269° C.) and 2-hydroxyethyl-amine.

Melting point: 228°–230° C. (methanol).

EXAMPLE 62

8-(4-Bromophenyl-thio)-2-diethanolamino-4-(1-oxido-thiomorpholino)-pyrimido[5,4-d]pyrimidine This compound was prepared analogous to Example 1 from 8-(4-bromophenyl-thio)-2-chloro-4-(1-oxidothiomorpholino)-pyrimido[5,4-d]pyrimidine (melting point: 272°–275° C.) and diethanolamine.

Melting point: 176°–178° C. (ethyl acetate/methanol).

EXAMPLE 63

8-Benzylthio-4-(2,6-dimethyl-morpholino)-2-(2-hydroxyethylamino)-pyrimido[5,4-d]pyrimidine This compound was prepared analogous to Example 1 from 8-benzylthio-2-chloro-4-(2,6-dimethylmorpholino)pyrimido[5,4-d]pyrimidine (melting point: 85°–90° C.) and 2-hydroxyethyl-amine.

Melting point: 96°–99° C. (ethanol).

EXAMPLE 64

8-Amino-2-(2-hydroxyethyl-amino)-4-(1-oxido-thiomorpholino)pyrimido[5,4-d]pyrimidine This compound was prepared analogous to Example 2 from 8-amino-2-chloro-4-(1-oxido-thiomorpholino)-pyrimido[5,4-d]pyrimidine (melting point: 270°–272° C.; decomposition) and 2-hydroxyethyl-amine.

Melting point: 221°–223° C. (reprecipitation from 0.1 N hydrochloric acid with ammonia).

EXAMPLE 65

2-(2-Hydroxyethyl-amino)-8-methylamino-4-(1-oxido-thiomorpholino)-pyrimido[5,4-d]pyrimidine This compound was prepared analogous to Example 2 from 2-chloro-8-methylamino-4-(1-oxido-thiomorpholino)pyrimido[5,4-d]pyrimidine (melting point: 278°–280° C.) and 2-hydroxyethyl-amine.

Melting point: 175°–177° C. (dioxane).

EXAMPLE 66

2-(2-Hydroxyethyl-amino)-4-(1-oxido-thiomorpholino)-8-propylamino-pyrimido[5,4-d]pyrimidine This compound was prepared analogous to Example 2 from 2-chloro-4-(1-oxido-thiomorpholino)-8-propylaminopyrimido[5,4-d]pyrimidine (melting point: 174°–176° C.) and 2-hydroxyethyl-amine.

Melting point: 164°–166° C. (methanol).

EXAMPLE 67

2-(2-Hydroxyethyl-amino)-8-isopropylamino-4-(1-oxidothiomorpholino)-pyrimido[5,4-d]pyrimidine This compound was prepared analogous to Example 2 from 2-chloro-8-isopropylamino-4-(1-oxido-thiomorpholino)pyrimido[5,4-d]pyrimidine (melting point: 213°–215° C.) and 2-hydroxyethyl-amine.

Melting point: 154°–156° C. (ethyl acetate).

EXAMPLE 68

8-Butylamino-2-(2-hydroxyethyl-amino)-4-(1-oxidothiomorpholino)-pyrimido[5,4-d]pyrimidine This compound was prepared analogous to Example 2 from 8-butylamino-2-chloro-4-(1-oxido-thiomorpholino)pyrimido[5,4-d]pyrimidine (melting point: 179°–181° C.) and 2-hydroxyethyl-amine.

Melting point: 157°–159° C. (methanol).

EXAMPLE 69

2-(2-Hydroxyethyl-amino)-8-isopentylamino-4-(1-oxidothiomorpholino)-pyrimido[5,4-d]pyrimidine This compound was prepared analogous to Example 2 from 2-chloro-8-isopentylamino-4-(1-oxido-thiomorpholino)pyrimido[5,4-d]pyrimidine (melting point: 176°–178° C.) and 2-hydroxyethyl-amine.

Melting point: 173°–174° C. (ethyl acetate).

EXAMPLE 70

2-(2-Hydroxyethyl-amino)-8-octylamino-4-(1-oxidothiomorpholino)-pyrimido[5,4-d]pyrimidine This compound was prepared analogous to Example 2 from 2-chloro-8-octylamino-4-(1-oxido-thiomorpholino)-pyrimido[5,4-d]pyrimidine (melting point: 145°–147° C.) and 2-hydroxyethylamine.

Melting point: 137°–139° C. (methanol).

EXAMPLE 71

8-(N-Ethyl-butylamino)-2-(2-hydroxyethyl-amino)-4-(1-oxidothiomorpholino)-pyrimido[5,4-d]pyrimidine This compound was prepared analogous to Example 2 from 8-(N-ethyl-butylamino)-2chloro-4-(1-oxido-thiomorpholino)pyrimido[5,4-d]pyrimidine (melting point: 157°–158° C.) and 2-hydroxyethyl-amine.

Melting point: 154°–156 ° C. (methanol).

EXAMPLE 72

8-Dibutylamino-2-(2-hydroxyethyl-amino)-4-(1-oxido-thiomorpholino)-pyrimido[5,4-d]pyrimidine This compound was prepared analogous to Example 2 from 2-chloro-8-dibutylamino-4-(1-oxido-thiomorpholino)pyrimido[5,4-d]pyrimidine (melting point: 187°–189° C.) and 2-hydroxyethyl-amine).

Melting point: 175°–177° C. (methanol).

EXAMPLE 73

8-(N-Cyclohexyl-methylamino)-2-(2-hydroxyethyl-amino)-4-(1-oxido-thiomorpholino)-pyrimido[5,4-d]pyrimidine This compound was prepared analogous to Example 2 from 2-chloro-8-(N-cyclohexyl-methylamino)-4-(1-oxidothiomorpholino)-pyrimido[5,4-d]pyrimidine (melting point: 226°–228° C.) and 2-hydroxyethyl-amine.

Melting point: 222°–223° C. (methanol).

EXAMPLE 74

8-(Cyclohexylmethyl-amino)-2-(2-hydroxyethyl-amino)-4-(1-oxido-thiomorpholino)-pyrimido[5,4-d]pyrimidine This compound was prepared analogous to Example 2 from 2-chloro-8-cyclohexylmethyl-amino-4-(1-oxido-thiomorpholino)-pyrimido[5,4-d]pyrimidine (melting point: 217°–218° C.) and 2-hydroxyethyl-amine.

Melting point: 155°–156° C. (methanol).

EXAMPLE 75

8-Benzylamino-2-(2-hydroxyethyl-amino)-4-(1-oxidothiomorpholino)-pyrimido[5,4-d]pyrimidine This compound was prepared analogous to Example 2 from 8-benzylamino-2-chloro-4-(1-oxido-thiomorpholino)pyrimido[5,4-d]pyrimidine (melting point: 232°–233° C.) and 2-hydroxyethyl-amine.

Melting point: 192°–194° C. (ethanol/dioxane).

Melting point of the maleate: 170°–175° C.

EXAMPLE 76

8-Benzylamino-2-(2-hydroxyethyl-amino)-4-morpholinopyrimido[5,4-d]pyrimidine

This compound was prepared analogous to Example 2 from 8-benzylamino-2-chloro-4-morpholino-pyrimido[5,4-d]pyrimidine (melting point: 139°–141° C.) and 2-hydroxyethylamine.

Melting point: 130°–132° C.

EXAMPLE 77

8-Benzylamino-2-(2-hydroxyethyl-amino)-4-thiomorpholinopyrimido[5,4]d]pyrimidine This compound was prepared analogous to Example 2 from 8-benzylamino-2-chloro-4-thiomorpholinopyrimido[5,4-d]pyrimidine (melting point: 129°–130° C.) and 2-hydroxyethylamine.

Melting point: 109°–111° C.

EXAMPLE 78

8-Benzylamino-2-(2-hydroxyethyl-amino)-4-(1,1-dioxidothiomorpholino)-pyrimido[5,4-d]pyrimidine This compound was prepared analogous to Example 2 from 8-benzylamino-2-chloro-4-(1,1-dioxido-thiomorpholino)pyrimido[5,4-d]pyrimidine (melting point: 213°–215° C.) and 2-hydroxyethyl-amine.

Melting point: 204°–205° C.

This compound was also obtained from 8-benzylamino-2-(2-hydroxyethyl-amino)-4-thiomorpholino-pyrimido[5,4-d]pyrimidine by oxidation with potassium permanganate in dilute hydrochloric acid.

EXAMPLE 79

8-Benzylamino-2-diethanolamino-4-(1-oxido-thiomorpholino)pyrimido[5,4-d]pyrimidine This compound was prepared analogous to Example 3 from 8-benzylamino-2-chloro-4-(1-oxido-thiomorpholino)pyrimido[5,4-d]pyrimidine (melting point: 232°–233° C.) and diethanolamine.

Melting point: 195°–196° C. (methanol).

EXAMPLE 80

8-Benzylamino-2-[N-(2-hydroxy-ethyl)-N-(2-methoxy-ethyl)amino]-4-(1-oxido-thiomorpholino)-pyrimido[5,4-d]pyrimidine This compound was prepared analogous to Example 3 from 8-benzylamino-2-chloro-4-(1-oxido-thiomorpholino)pyrimido[5,4-d]pyrimidine and N-(2-hydroxy-ethyl)-N-(2-methoxy-ethyl)-amine.

Melting point: 145°–147° C. (methanol).

EXAMPLE 81

2-Diethanolamino-4-(1-oxido-thiomorpholino)-8-phenethylamino-pyrimido[5,4-d]pyrimidine This compound was prepared analogous to Example 3 from 2-chloro-4-(1-oxido-thiomorpholino)-8-phenethylaminopyrimido[5,4-d]pyrimidine (melting point: 202°–204° C.) and diethanolamine.

Melting point: 194°–196° C. (methanol).

EXAMPLE 82

2-[N-(2-Hydroxy-ethyl)-N-(2-methoxy-ethyl)-amino]-4-(1-oxido-thiomorpholino)-8-phenethylamino-pyrimido[5,4-d]pyrimidine This compound was prepared analogous to Example 3 from 2-chloro-4-(1-oxido-thiomorpholino)-8-phenethylaminopyrimido[5,4-d]pyrimidine and N-(2-hydroxyethyl)-2-methoxyethylamine.

Melting point: 115°–117° C. (methanol/water).

EXAMPLE 83

2-Diethanolamino-4-(1-oxido-thiomorpholino)-8-(3-phenylpropylamino)-pyrimido[5,4-d]pyrimidine This compound was prepared analogous to Example 3 from 2-chloro-4-(1-oxido-thiomorpholino)-8-(3-phenylpropylamino)-pyrimido[5,4-d]pyrimidine (melting point: 152°–154° C.) and diethanolamine.

Melting point: 164°–166° C. (ethyl acetate/methanol).

EXAMPLE 84

2-(2-Hydroxyethyl-amino)-4-(1-oxido-thiomorpholino)-8-phenethylamino-pyrimido[5,4-d]pyrimidine This compound was prepared analogous to Example 2 from 2-chloro-4-(1-oxido-thiomorpholino)-8-phenethylaminopyrimido[5,4-d]pyrimidine (melting point: 202°–204° C.) and 2-hydroxyethyl-amine.

Melting point: 187°–189° C. (methanol).
Melting point of the hydrochloride: 161°–164° C.
Melting point of the maleate: 156°–158° C.

EXAMPLE 85

2-(2-Hydroxyethyl-amino)-4-(1-oxido-thiomorpholino)-8-(3-phenylpropyl-amino)-pyrimido[5,4-d]pyrimidine This compound was prepared analogous to Example 2 from 2-chloro-4-(1-oxido-thiomorpholino)-8-(3-phenylpropylamino)-pyrimido[5,4-d]pyrimidine (melting point: 152°–154° C.) and 2-hydroxyethyl-amine.

Melting point: 164°–166° C. (methanol).

EXAMPLE 86

2-(2-Hydroxyethyl-amino)-4-)1-oxido-thiomorpholino)-8-(4-phenylbutyl-amino)-pyrimido[5,4-d]pyrimidine This compound was prepared analogous to Example 2 from 2-chloro-4-(1-oxido-thiomorpholino)-8-(4-phenylbutylamino)-pyrimido[5,4-d]pyrimidine (melting point: 156°–158° C.) and 2-hydroxyethyl-amine.

Melting point: 164°–166° C. (ethyl acetate).

EXAMPLE 87

2-(2-Hydroxyethyl-amino)-4-(1-oxido-thiomorpholino)-8-(L-1-phenylethyl-amino)-pyrimido[5,4-d]pyrimidine This compound was prepared analogous to Example 2 from 2-chloro-4-(1-oxido-thiomorpholino)-8-(L-1-phenylethyl-amino)-pyrimido[5,4-d]pyrimidine (melting point: 167°–169° C.) and 2-hydroxyethyl-amine.

Melting point: 85°–88° C.

EXAMPLE 88

8-Benzylamino-2-(5-hydroxypentyl-amino)-4-(1-oxido-thiomorpholino)-pyrimido[5,4-d]pyrimidine This compound was prepared analogous to Example 2 from 8-benzylamino-2-chloro-4-(1-oxido-thiomorpholino)pyrimido[5,4-d]pyrimidine (melting point: 232°–233° C.) and 5-amino-1-pentanol.

Melting point: 132°–134° C. (methanol).

EXAMPLE 89

8-Benzylamino-2-(5-hydroxy-1,5-dimethylhexyl-amino)-4-(1-oxido-thiomorpholino)-pyrimido[5,4-d]pyrimidine This compound was prepared analogous to Example 3 from 8-benzylamino-2-chloro-4-(1-oxido-thiomorpholino)-pyrimido[5,4-d]pyrimidine (melting point: 232°–233° C.) and 6-amino2-methyl-2-heptanol. Resin.

EXAMPLE 90

8-Benzylamino-2-(3-hydroxy-piperidino)-4-(1-oxidothiomorpholino)-pyrimido[5,4-d]pyrimidine This compound was prepared analogous to Example 2 from 8-benzylamino-2-chloro-4-(1-oxido-thiomorpholino)-pyrimido[5,4-d]pyrimidine (melting point: 232°–233° C.) and 3-hydroxypiperidine.

Melting point: 213°–215° C. (ethanol).

EXAMPLE 91

8-(N-Benzyl-methylamino)-2-diethanolamino-4-(1-oxidothiomorpholino)-pyrimido[5,4-d]pyrimidine This compound was prepared analogous to Example 3 from 8-(N-benzyl-methylamino)-2-chloro-4-(1-oxidothiomorpholino)-pyrimido[5,4-d]pyrimidine (melting point: 158°–160° C.) and diethanolamine.

Melting point: 159°–161° C. (methanol).

EXAMPLE 92

8-(N-Benzyl-methylamino)-2-(2-hydroxyethyl-amino)-4-thiomorpholino-pyrimido[5,4-d]pyrimidine This compound was prepared analogous to Example 2 from 8-(N-benzylmethylamino)-2-chloro-4-thiomorpholinopyrimido[5,4-d]pyrimidine (melting point: 95°–97° C.) and 2-hydroxyethyl-amine.

Melting point: 112°–114° C.

EXAMPLE 93

8-(N-Benzyl-methylamino)-2-(2-hydroxyethyl-amino)-4-morpholino-pyrimido[5,4-d]pyrimidine This compound was prepared analogous to Example 2 from 8-(N-benzyl-methylamino)-2-chloro-4-morpholinopyrimido[5,4-d]pyrimidine (melting point: 121°–123° C.) and 2-hydroxyethyl-amine.

Melting point: 106°–108° C. (methanol).

EXAMPLE 94

8-(N-Ethyl-benzylamino)-2-(2-hydroxyethyl-amino)-4-(1-oxidothiomorpholino)-pyrimido[5,4-d]pyrimidine This compound was prepared analogous to Example 2 from 8-(N-ethyl-benzylamino)-2-chloro-4-(1-oxidothiomorpholino)-pyrimido[5,4-d]pyrimidine (melting point: 163°–165° C.) and 2-hydroxyethyl-amine.

Melting point: 164°–165° C. (methanol).

EXAMPLE 95

8-(N-Benzyl-propylamino)-2-(2-hydroxyethyl-amino)-4-(1-oxido-thiomorpholino)-pyrimido[5,4-d]pyrimidine This compound was prepared analogous to Example 2 from 8-(N-benzyl-propylamino)-2-chloro-4-(1-oxido-thiomorpholino)-pyrimido[5,4-d]pyrimidine (melting point: 183°–184° C.) and 2-hydroxyethyl-amine.

Melting point: 167°–169° C. (ethyl acetate).

EXAMPLE 96

8-(N-Benzyl-butylamino)-2-(2-hydroxyethyl-amino)-4-(1-oxido-thiomorpholino)-pyrimido[5,4-d]pyrimidine This compound was prepared analogous to Example 2 from 8-(N-benzyl-butylamino)-2-chloro-4-(1-oxido-thiomorpholino)-pyrimido[5,4-d]pyrimidine (melting point: 153°–155° C.) and 2-hydroxyethyl-amine.

Melting point: 162°–163° C. (reprecipitation from 2 N hydrochloric acid with ammonia).

EXAMPLE 97

8-[N-Benzyl-N-(2-hydroxy-ethyl)-amino]-2-(2-hydroxyethylamino)-4-(1-oxidothiomorpholino)-pyrimido[5,4-d]-pyrimidine This compound was prepared analogous to Example 2 from 8-[N-benzyl-N-(2-hydroxyethyl)-amino]-2-chloro-4-(1-oxido-thiomorpholino)-pyrimido[5,4-d]pyrimidine (melting point: 153°–155° C.) and 2-hydroxyethyl-amine.

Melting point: 140°–142° C. (ethyl acetate/methanol).

EXAMPLE 98

2,8-Bis(2-hydroxyethyl-amino)-4-(1-oxido-thiomorpholino)pyrimido[5,4-d-pyrimidine This compound was prepared analogous to Example 2 from 2,8-dichloro-4-(1-oxido-thiomorpholino)-pyrimido[5,4-d]pyrimidine (melting point: 195°–198° C.) and 2-hydroxyethyl-amine.

Melting point: 156°–158° C. (water).

EXAMPLE 99

2-(2-Hydroxyethyl-amino)-8-(5-hydroxypentyl-amino)-4-(1-oxido-thiomorpholino)-pyrimido[5,4-d]pyrimidine This compound was prepared analogous to Example 2 from 2-chloro-8-(5-hydroxypentyl-amino)-4-(1-oxidothiomorpholino)-pyrimido[5,4-d]pyrimidine (melting point: 202°–204° C.) and 2-hydroxyethyl-amine.

Melting point: 121°–123° C. (reprecipitation from 0.1 N hydrochloric acid with ammonia).

EXAMPLE 100

2(2-Hydroxyethyl-amino)-8-(5-hydroxy-1,5-dimethylhexylamino)-4-(1-oxido-thiomorpholino)-pyrimido[5,4-d]pyrimidine This compound was prepared analogous to Example 2 from 2-chloro-8-(5-hydroxy-1,5-dimethylhexylamino)-4-(1-oxido-thiomorpholino)-pyrimido[5,4-d]pyrimidine (resin) and 2-hydroxyethyl-amine. Resin.

EXAMPLE 101

8-(3-Ethoxypropyl-amino)-2-(2-hydroxyethyl-amino)-4-(1-oxido-thiomorpholino)-pyrimido[5,4-d]pyrimidine This compound was prepared analogous to Example 2 from 8-(3-ethoxypropyl-amino)-2-chloro-4-(1-oxido-thiomorpholino)-pyrimido[5,4-d]pyrimidine (melting point: 153°–154° C.) and 2-hydroxyethyl-amine.

Melting point: 149°–151° C. (ethyl acetate).

EXAMPLE 102

8-Furfurylamino-2-(2-hydroxyethyl-amino)-4-(1-oxidothiomorpholino)-pyrimido[5,4-d]pyrimidine This compound was prepared analogous to Example 2 from 2-chloro-8-furfurylamino-4-(1-oxido-thiomorpholino)pyrimido[5,4-d]pyrimidine (melting point: 203–205° C.) and 2-hydroxyethyl-amine.

Melting point: 194°–196° C. (methanol).

EXAMPLE 103

2-(2-Hydroxypropyl-amino)-4-(1-oxido-thiomorpholino)-8-(3-picolyl-amino)-pyrimido[5,4-d]pyrimidine This compound was prepared analogous to Example 2 from 2-chloro-4-(1-oxido-thiomorpholino)-8-(3-picolyl-amino)pyrimido[5,4-d]pyrimidine (melting point: 227°–229° C.) and 1-amino-2-propanol.

Melting poing: 197°–199° C. (reprecipitation from 0.1 N hydrochloric acid with ammonia).

EXAMPLE 104

2-(2-Hydroxyethyl-amino)-8-[N-methyl-N-(3-picolyl)-amino]4-(1-oxido-thiomorpholino)-pyrimido[5,4-d]pyrimidine This compound was prepared analogous to Example 2 from 2-chloro-8-[N-methyl-N-(3-picolyl)-amino]-4-(1- oxidothiomorpholino)-pyrimido[5,4-d]pyrimidine (melting point: 154°–156° C.) and 2-hydroxyethyl-amine.

Melting point: 186°–188° C. (reprecipitation from 0.1 N hydrochloric acid by means of ammonia).

EXAMPLE 105

2-(2-Hydroxyethyl-amino)-8-(N-methyl-anilino)-4-(1-oxidothiomorpholino)-pyrimido[5,4-d]pyrimidine This compound was prepared analogous to Example 2 from 2-chloro-8-(N-methyl-anilino)-4-(1-oxido-thiomorpholino)pyrimido[5,4-d]pyrimidine (melting point: 237°–239° C.) and 2-hydroxyethyl-amine.

Melting point: 217°–219° C. (reprecipitation from 0.1 N hydrochloric acid with ammonia).

EXAMPLE 106

8-(4-Ethoxy-anilino)-2-(2-hydroxyethyl-amino)-4-(1-oxidothiomorpholino)-pyrimido[5,4-d]pyrimidine This compound was prepared analogous to Example 3 from 8-(4-ethoxy-anilino)-2-chloro-4-(1-oxido-thiomorpholino) pyrimido[5,4-d]pyrimidine (melting point: 237°–240° C.) and 2-hydroxyethyl-amine.

Melting point: 219°–221° C.

EXAMPLE 107

2-(2-Hydroxyethyl-amino)-4-(1-oxido-thiomorpholino)-8-(3-trifluoromethyl-anilino)-pyrimido[5,4-d]pyrimidine from 2-chloro-4-(1-oxido-thiomorpholino)-8-(3-trifluoromethyl-anilino)-pyrimido[5,4-d]pyrimidine (melting point: 215°–218° C.) and 2-hydroxyethyl-amine.

Melting point: 233°–235° C. (ethanol).

EXAMPLE 108

2-(2-Hydroxyethyl-amino)-8-(4-methylbenzyl-amino)-4-(1-oxido-thiomorpholino)-pyrimido[5,4-d]pyrimidine This compound was prepared analogous to Example 2 from 2-chloro-8-(4-methylbenzyl-amino)-4-(1-oxido-thiomorpholino)-pyrimido[5,4-d]pyrimidine (melting point: 185°–187° C.) and 2-hydroxyethyl-amine.

Melting point: 173°–175° C. (ethyl acetate).

EXAMPLE 109

2-(2-Hydroxyethyl-amino)-8-(3-methoxybenzyl-amino)-4-(1-oxido-thiomorpholino)-pyrimido[5,4-d]pyrimidine This compound was prepared analogous to Example 2 from 2-chloro-8-(3-methoxybenzyl-amino)-4-(1-oxido-thiomorpholino)-pyrimido[5,4-d]pyrimidine (melting point: 222°–224° C.) and 2-hydroxyethyl-amine.

Melting point: 168°–170° C. (ethyl acetate/dioxane).

EXAMPLE 110

2-(2-Hydroxyethyl-amino)-8-(4-methoxybenzyl-amino)-4-(1-oxido-thiomorpholino)-pyrimido[5,4-d]pyrimidine This compound was prepared analogous to Example 2 from 2-chloro-8-(4-methoxybenzyl-amino)-4-(1-oxido-thiomorpholino) pyrimido[5,4-d]pyrimidine (melting point: 220°–222° C.) and 2-hydroxyethyl-amine.

Melting point: 173°–175° C. (ethyl acetate/dioxane).

EXAMPLE 111

8-(3,4-Dimethoxybenzyl-amino)-2-(2-hydroxyethyl-amino)-4-1-oxido-thiomorpholino)-pyrimido[5,4-d]pyrimidine This compound was prepared analogous to Example 2 from 2-chloro-8-(3,4-dimethoxybenzyl-amino)-4-(oxido-thiomorpholino)-pyrimido[5,4-d]pyrimidine (melting point: 218°–220° C.) and 2-hydroxyethyl-amine.

Melting point: 175°–177° C. (methanol).

EXAMPLE 112

2-(2-Hydroxyethyl-amino)-8-(3,4-methylenedioxybenzyl-amino)-4-(1-oxido-thiomorpholino)-pyrimido[5,4-d]pyrimidine This compound was prepared analogous to Example 2 from 2-chloro-8-(3,4-methylenedioxybenzyl-amino)-4-(1-oxidothiomorpholino)-pyrimido[5,4-d]pyrimidine (melting point: 239°–241° C.) and 2-hydroxyethyl-amine.

Melting point: 216°–218° C. (dioxane).

EXAMPLE 113

8-(4-Fluorobenzyl-amino)-2-(2-hydroxyethyl-amino)-4-(1-oxido-thiomorpholino)-pyrimido[5,4-d]pyrimidine This compound was prepared analogous to Example 2 from 2-chloro-8-(4-fluorobenzyl-amino)-4-(1-oxido-thiomorpholino)-pyrimido[5,4-d]pyrimidine (melting point: 210°–212° C.) and 2-hydroxyethyl-amine.

Melting point: 190°–192° C. (ethyl acetate/methanol).

EXAMPLE 114

8-(2-Chlorobenzyl-amino)-2-(2-hydroxyethyl-amino)-4-(1-oxido-thiomorpholino)-pyrimido[5,4-d]pyrimidine This compound was prepared analogous to Example 2 from 2-chloro-8-(2-chlorobenzyl-amino)-4-(1-oxido-thiomorpholino)-pyrimido[5,4-d]pyrimidine (melting point: 238°–240° C.) and 2-hydroxyethyl-amine.

Melting point: 178°–180° C. (methanol).

EXAMPLE 115

8-(3-Chlorobenzyl-amino)-2-(2-hydroxyethyl-amino)-4-(1-oxido-thiomorpholino)-pyrimido[5,4-d]pyrimidine This compound was prepared analogous to Example 2 from 2-chloro-8-(3-chlorobenzyl-amino)-4-(1-oxido-thiomorpholino)-pyrimido[5,4-d]pyrimidine (melting point: 239°–241° C.) and 2-hydroxyethyl-amine.

Melting point: 203°–204° C. (dioxane).

EXAMPLE 116

8-(4-Chlorobenzyl-amino)-2-(2-hydroxyethyl-amino)-4-(1-oxido-thiomorpholino)-pyrimido[5,4-d]pyrimidine This compound was prepared analogous to Example 2 from 2-chloro-8-(4-chlorobenzyl-amino)-4-(1-oxido-thiomorpholino)-pyrimido[5,4-d]pyrimidine (melting point: 216°–218° C.) and 2-hydroxyethyl-amine.

Melting point: 215°–217° C. (dioxane).

EXAMPLE 117

8-(2,4-Dichlorobenzyl-amino)-2-(2-hydroxyethyl-amino)-4-(1-oxido-thiomorpholino)-pyrimido[5,4-d]pyrimidine This compound was prepared analogous to Example 2 from 2-chloro-8-(2,4-dichlorobenzyl-amino)-4-(1-oxidothiomorpholino)-pyrimido[5,4-d]pyrimidine (melting point: 196°–198° C.) and 2-hydroxyethyl-amine.

Melting point: 210°–212° C. (dioxane).

EXAMPLE 118

8-(3,4-Dichlorobenzyl-amino)-2-(2-hydroxyethyl-amino)-4-(1-oxido-thiomorpholino)-pyrimido[5,4-d]pyrimidine This compound was prepared analogous to Example 2 from 2-chloro-8-(3,4-dichlorobenzyl-amino)-4-(1-oxidothiomorpholino)-pyrimido[5,4-d]pyrimidine (melting point: 259°–261° C.) and 2-hydroxyethyl-amine.

Melting point: 186°–188° C. (dioxane).

EXAMPLE 119

8-(3,4-Dimethoxyphenethyl-amino)-2-(2-hydroxyethyl-amino)-4-(1-oxido-thiomorpholino)-pyrimido[5,4-d]pyrimidine This compound was prepared analogous to Example 2 from 2-chloro-8-(3,4-dimethoxyphenethyl-amino)-4-(1-oxidothiomorpholino)-pyrimido[5,4-d]pyrimidine (melting point: 214°–216° C.) and 2-hydroxyethyl-amine.

Melting point: 168°–170° C. (reprecipitation from 2N hydrochloric acid with ammonia.

EXAMPLE 120

8-[N-(3,4-dimethoxy-phenethyl)-methylamino]-2-(2-hydroxyethyl-amino)-4-(1-oxido-thiomorpholino)-pyrimido[5,4-d]pyrimidine This compound was prepared analogous to Example 2 from 2-chloro-8-[N-(3,4-dimethoxy-phenethyl)-methylamino]-4-(1-oxido-thiomorpholino)-pyrimido[5,4-d]pyrimidine (melting point: 178°–179° C.) and 2-hydroxyethyl-amine.

Melting point: 153°–154° C. (ethyl acetate).

EXAMPLE 121

2-(2-Hydroxyethyl-amino)-4-(1-oxido-thiomorpholino)-8-piperidino-pyrimido[5,4-d]pyrimidine This compound was prepared analogous to Example 3 from 2-chloro-4-(1-oxido-thiomorpholino)-8-piperidinopyrimido[5,4-d]pyrimidine (melting point: 203°–204° C.) and 2-hydroxyethyl-amine.

Melting point: 165°–167° C.

EXAMPLE 122

2-(3-Hydroxypropyl-amino)-4-(1-oxido-thiomorpholino)-8-piperidino-pyrimido[5,4-d]pyrimidine This compound was prepared analogous to Example 3 from 2-chloro-4-(1-oxido-thiomorpholino)-8-piperidinopyrimido[5,4-d]pyrimidine and 3-hydroxypropyl-amine.

Melting point: 142°–144° C. (ethyl acetate).

EXAMPLE 123

2-(2-Hydroxypropyl-amino)-4-(1-oxido-thiomorpholino)-8-piperidino-pyrimido[5,4-d]pyrimidine This compound was prepared analogous to Example 3 from 2-chloro-4-(1-oxido-thiomorpholino)-8-piperidinopyrimido[5,4-d]pyrimidine and 2-hydroxypropyl-amine.

Melting point: 175°–177° C. (ethyl acetate).

EXAMPLE 124

2-(2,2-Dimethyl-3-hydroxypropyl-amino)-4-(1-oxido-thiomorpholino)-8-piperidino-pyrimido[5,4-d]pyrimidine This compound was prepared analogous to Example 3 from 2-chloro-4-(1-oxido-thiomorpholino)-8-piperidinopyrimido[5,4-d]pyrimidine and 2,2-dimethyl-3-hydroxypropylamine.

Melting point: 192°–194° C. (ethanol).

EXAMPLE 125

2-(2,3-Dihydroxypropyl-amino)-4-(1-oxido-thiomorpholino)-8-piperidino-pyrimido[5,4-d]pyrimidine This compound was prepared analogous to Example 3 from 2-chloro-4-(1-oxido-thiomorpholino)-8-piperidinopyrimido[5,4-d]and 2,3-dihydroxypropylamine.

Melting point: 189°–190° C. (ethanol).

EXAMPLE 126

2-[N-(2-Hydroxy-ethyl)-N-(2-methoxy-ethyl)-amino]-4-(1-oxido-thiomorpholino)-8-piperidino-pyrimido[5,4-d]pyrimidine This compound was prepared analogous to Example 3 from 2-chloro-4-(1-oxido-thiomorpholino)-8-piperidinopyrimido[ 5,4-d]pyrimidine and N-(2-hydroxy-ethyl)-N-(2-methoxy-ethyl)-amine.

Melting point: 133°–135° C. (ethyl acetate).

EXAMPLE 127

2-(2-Hydroxyethyl-amino)-4-(1-oxido-thiomorpholino)-8-pyrrolidino-pyrimido[5,4-d]pyrimidine This compound was prepared analogous to Example 3 from 2-chloro-4-(1-oxido-thiomorpholino)-8-pyrrolidinopyrimido[5,4-d]pyrimidine (melting point: 243°–244° C.) and 2-hydroxyethyl-amine.

Melting point: 200°–203° C.

EXAMPLE 128

8-Hexamethyleneimino-2-(2-hydroxyethyl-amino)-4-(1-oxidothiomorpholino)-pyrimido[5,4-d]pyrimidine This compound was prepared analogous to Example 3 from 2-chloro-8-hexamethylene-imino-4-(1-oxido-thiomorpholino)-pyrimido[5,4-d]pyrimidine (melting point: 206°–207° C.) and 2-hydroxyethyl-amine.

Melting point: 190°–192° C. (ethyl acetate).

EXAMPLE 129

2-Diethanolamino-8-heptamethyleneimino-4-(1-oxido-thiomorpholino)-pyrimido[5,4-d]pyrimidine This compound was prepared analogous to Example 3 from 2-chloro-8-heptamethyleneimino-4-(1-oxido-thiomorpholino)-pyrimido[5,4-d]pyrimidine (melting point: 214°–215° C.) and diethanolamine.

Melting point: 186°–188° C. (ethanol).

EXAMPLE 130

2-Diethanolamino-8-(4-methyl-piperidino)-4-(1-oxido-thiomorpholino)-pyrimido[5,4-d]pyrimidine This compound was prepared analogous to Example 3 from 2-chloro-8-(4-methyl-piperidino)-4-(1-oxido-thiomorpholino)-pyrimido[5,4-d]pyrimidine (melting point: 195°–196° C.) and diethanolamine.

Melting point: 175°–177° C. (ethanol).

EXAMPLE 131

2-Diethanolamino-8-(3,5-dimethyl-piperidino)-4-(1-oxidothiomorpholino)-pyrimido[5,4-d]pyrimidine This compound was prepared analogous to Example 3 from 2-chloro-8-(3,5-dimethyl-piperidino)-4-(1-oxido-thiomorpholino)-pyrimido[5,4-d]pyrimidine (melting point: 186°–187° C.) and diethanolamine.

Melting point: 215°–217° C. (ethanol).

EXAMPLE 132

8-(2-Ethyl-piperidino)-2-diethanolamino-4-(1-oxido-thiomorpholino)-pyrimido[5,4-d]pyrimidine This compound was prepared analogous to Example 3 from 8-(2-ethyl-piperidino)-2-chloro-4-(1-oxido-thiomorpholino)-pyrimido[5,4-d]pyrimidine (melting point: 171°–174° C.) and diethanolamine.

Melting point: 140°–142° C. (ethyl acetate).

EXAMPLE 133

2-Diethanolamino-4-(1-oxido-thiomorpholino)-8-(1,2,5,6-tetrahydro-pyridino)-pyrimido[5,4-d]pyrimidine This compound was prepared analogous to Example 3 from 2-chloro-4-(1-oxido-thiomorpholino)-8-(1,2,5,6-tetrahydro-pyridino)-pyrimido[5,4-d]pyrimidine (melting point: 189°–190° C.) and diethanolamine.

Melting point: 140°–143° C. (ethanol).

EXAMPLE 134

8-[N,N-Bis-(2-methoxy-ethyl)-amino]-2-diethanolamino-4-(1-oxido-thiomorpholino)-pyrimido[5,4-d]pyrimidine This compound was prepared analogous to Example 3 from 8-[N,N-bis-(2-methoxy-ethyl)-amino]-2-chloro-4-(1-oxido-thiomorpholino)-pyrimido[5,4-d]pyrimidine (melting point: 136°–138° C.) and diethanolamine.

Melting point: 120°–122° C. (ethyl acetate).

EXAMPLE 135

2-Diethanolamino-8-methoxy-4-(1-oxido-thiomorpholino)-pyrimido[5,4-d]pyrimidine

This compound was prepared analogous to Example 4 from 2-chloro-8-methoxy-4-(1-oxido-thiomorpholino)-pyrimido[5,4-d]pyrimidine (melting point: 218°–221° C.) and diethanolamine.

Melting point: 198°–200° C. (dioxane).

EXAMPLE 136

2-Diethanolamino-8-methoxy-4-morpholino-pyrimido[5,4-d]pyrimidine

This compound was prepared analogous to Example 4 from 2-chloro-8-methoxy-4-morpholino-pyrimido[5,4-d]pyrimidine (melting point: 160°–162° C.) and diethanolamine.

Melting point: 172°–174° C. (water).

EXAMPLE 137

2-Diethanolamino-4-(1-oxido-thiomorpholino)-8-propoxypyrimido[5,4-d]pyrimidine

This compound was prepared analogous to Example 4 from 2-chloro-4-(1-oxido-thiomorpholino)-8-propoxy-pyrimido[5,4-d]pyrimidine (melting point: 205°–207° C.) and diethanolamine.

Melting point: 195°–197° C. (ethyl acetate).

EXAMPLE 138

2-Diethanolamino-8-isopentyloxy-4-(1-oxido-thiomorpholino)pyrimido[5,4-d]pyrimidine This compound was prepared analogous to Example 4 from 2-chloro-8-isopentyloxy-4-(1-oxido-thiomorpholino)pyrimido[5,4-d]pyrimidine (melting point: 143°–145° C.) and diethanolamine.

Melting point: 153°–155° C. (ethyl acetate).

EXAMPLE 139

2-Diethanolamino-8-octyloxy-4-(1-oxido-thiomorpholino)pyrimido[5,4-d]pyrimidine

This compound was prepared analogous to Example 4 from 2-chloro-8-octyloxy-4-(1-oxido-thiomorpholino)pyrimido[5,4-d]pyrimidine (melting point: 94°–96° C.) and diethanolamine.

Melting point: 128°–130° C. (ethyl acetate).

EXAMPLE 140

8-Cyclohexyloxy-2-diethanolamino-4-(1-oxido-thiomorpholino)pyrimido[5,4-d]pyrimidine This compound was prepared analogous to Example 4 from 2-chloro-8-cyclohexyloxy-4-(1-oxido-thiomorpholino)pyrimido[5,4-d]pyrimidine (melting point: 185°–187° C.) and diethanolamine.

Melting point: 217°–219° C. (ethanol).

EXAMPLE 141

8-Benzyloxy-2-(2-hydroxyethyl-amino)-4-(1-oxido-thiomorpholino)-pyrimido[5,4-d]pyrimidine This compound was prepared analogous to Example 4 from 8-benzyloxy-2-chloro-4-(1-oxido-thiomorpholino)pyrimido[5,4-d]pyrimidine (melting point: 227°–229° C.) and 2-hydroxyethyl-amine.

Melting point: 182°–184° C. (ethyl acetate/methanol).

EXAMPLE 142

8-Benzyloxy-2-(3-hydroxypropyl-amino)-4-(1-oxido-thiomorpholino)-pyrimido[5,4-d]pyrimidine This compound was prepared analogous to Example 4 from 8-benzyloxy-2-chloro-4-(1-oxido-thiomorpholino)pyrimido[5,4-d]pyrimidine and 3-hydroxypropyl-amine.

Melting point: 179°–181° C. (ethanol).

EXAMPLE 143

8-Benzyloxy-2-[N-(2-hydroxy-ethyl)-N-(5-hydroxypentyl)amino]-4-(1-oxido-thiomorpholino)-pyrimido[5,4-d]pyrimidine This compound was prepared analogous to Example 4 from 8-benzyloxy-2-chloro-4-(1-oxido-thiomorpholino)pyrimido[5,4-d]pyrimidine and N(2-hydroxyethyl)-N-(5-hydroxy-pentyl)-amine.

Melting point: 120°–122° C. (ethyl acetate).

EXAMPLE 144

8-Benzyloxy-2-(N-methyl-glucamino)-4-(1-oxido-thiomorpholino) pyrimido[5,4-d]pyrimidine This compound was prepared analogous to Example 4 from 8-benzyloxy-2-chloro-4-(1-oxido-thiomorpholino)pyrimido[5,4-d]pyrimidine and N-methyl-glucamine.

Melting point: 199°–201° C. (ethanol).

EXAMPLE 145

8-Benzyloxy-2-[N-(2-hydroxy-ethyl)-N-(2-methoxy-ethyl)amino]-4-(1-oxido-thiomorpholino)-pyrimido[5,4-d]pyrimidine This compound was prepared analogous to Example 4 from 8-benzyloxy-2-chloro-4-(1-oxido-thiomorpholino)pyrimido[5,4-d]pyrimidine and N-(2-hydroxy-ethyl)-N-(2-methoxy-ethyl)-amine.
Melting point: 110°–112° C. (methanol/water).

EXAMPLE 146

8-Benzyloxy-2-[N-(2-hydroxy-ethyl)-N-(2-hydroxy-propyl)amino]-4-(1-oxido-thiomorpholino)-pyrimido[5,4-d]pyrimidine This compound was prepared analogous to Example 4 from 8-benzyloxy-2-chloro-4-(1-oxido-thiomorpholino)pyrimido[5,4-d]pyrimidine and N-(2-hydroxyethyl)-N-(2-hydroxy-propyl)-amine.
Melting point: 148°–150° C. (ethyl acetate).

EXAMPLE 147

8-Benzyloxy-2-diisopropanolamino-4-(1-oxido-thiomorpholino)pyrimido[5,4-d]pyrimidine This compound was prepared analogous to Example 4 from 8-benzyloxy-2-chloro-4-(1-oxido-thiomorpholino)pyrimido[5,4-d]pyrimidine and diisopropanolamine.
Melting point: 199°–201° C. (ethyl acetate).

EXAMPLE 148

8-Benzyloxy-2-[N-(2-hydroxy-ethyl)-N-(2,3-dihydroxy-propyl)amino]-4-(1-oxido-thiomorpholino)-pyrimido[5,4-d]pyrimidine This compound was prepared analogous to Example 4 from 8-benzyloxy-2-chloro-4-(1-oxido-thiomorpholino)-pyrimido[5,4-d]pyrimidine and N-(2-hydroxy-ethyl)-N-(2,3-dihydroxy-propyl)-amine.
Melting point: 163°–165° C. (ethyl acetate).

EXAMPLE 149

8-Benzyloxy-2-(3-hydroxy-piperidino)-4-(1-oxido-thiomorpholino)-pyrimido[5,4-d]pyrimidine This compound was prepared analogous to Example 4 from 8-benzyloxy-2-chloro-4-(1-oxido-thiomorpholino)-pyrimido[5,4-d]pyrimidine and 3-hydroxy-piperidine.
Melting point: 210°–212° C. (ethanol).

EXAMPLE 150

2-(3-Hydroxypropyl-amino)-4-(1-oxido-thiomorpholino)-8-phenethoxy-pyrimido[5,4-d]pyrimidine This compound was prepared analogous to Example 4 from 2-chloro-4-(1-oxido-thiomorpholino)-8-phenethoxypyrimido[5,4-d]pyrimidine (melting point: 242°–245° C.) and 3-hydroxypropyl-amine in dimethylsulfoxide.
Melting point: 174°–176° C. (methanol).

EXAMPLE 151

2-Diethanolamino-4-(1-oxido-thiomorpholino)-8-phenethoxypyrimido[5,4-d]pyrimidine This compound was prepared analogous to Example 4 from 2-chloro-4-(1-oxido-thiomorpholino)-8-phenethoxypyrimido[5,4-d]pyrimidine and diethanolamine.
Melting point: 152°–154° C. (methanol).

EXAMPLE 152

2-(3-Hydroxy-piperidino)-4-(1-oxido-thiomorpholino)-8-phenethoxy-pyrimido[5,4-d]pyrimidine This compound was prepared analogous to Example 4 from 2-chloro-4-(1-oxido-thiomorpholino)-8-phenethoxypyrimido[5,4-d]pyrimidine and 3-hydroxy-piperidine.
Melting point: 192°–194° C. (methanol).

EXAMPLE 153

2-Diethanolamino-4-(1-oxido-thiomorpholino)-8-(3-phenyl-propoxy)-pyrimido[5,4-d]pyrimidine This compound was prepared analogous to Example 4 from 2-chloro-4-(1-oxido-thiomorpholino)-8-(3-phenyl-propoxy)pyrimido[5,4-d]pyrimidine (melting point: 152°–154° C.) and diethanolamine.
Melting point: 159°–161° C. (ethyl acetate).

EXAMPLE 154

2-Diethanolamino-4-(1-oxido-thiomorpholino)-8-(4-phenylbutoxy)-pyrimido[5,4-d]pyrimidine This compound was prepared analogous to Example 4 from 2-chloro-4-(1-oxido-thiomorpholino)-8-(4-phenylbutoxy)-pyrimido[5,4-d]pyrimidine (melting point: 124°–126° C.) and diethanolamine.
Melting point: 98°–100° C. (ethyl acetate).

EXAMPLE 155

8-Benzyloxy-2-diethanolamino-4-morpholino-pyrimido[5,4-d]pyrimidine

This compound was prepared analogous to Example 4 from 8-benzyloxy-2-chloro-4-morpholino-pyrimido[5,4-d]pyrimidine (melting point: 146°–148° C.) and diethanolamine.
Melting point: 167°–169° C. (ethyl acetate).

EXAMPLE 156

8-Benzyloxy-2-diethanolamino-4-thiomorpholino-pyrimido[5,4-d]pyrimidine

This compound was prepared analogous to Example 4 from 8-benzyloxy-2-chloro-4-thiomorpholino-pyrimido[5,4-d]pyrimidine (melting point: 183°–185° C.) and diethanolamine.
Melting point: 120°–122° C. (ethyl acetate).

EXAMPLE 157

8-Benzyloxy-2-dimethylamino-4-(1-oxido-thiomorpholino)pyrimido[5,4-d]pyrimidine

This compound was prepared analogous to Example 4 from 8-benzyloxy-2-chloro-4-(1-oxido-thiomorpholino)pyrimido[5,4-d]pyrimidine (melting point: 227°–229° C.) and dimethylamine under pressure.
Melting point: 202°–204° C. (ethanol).

EXAMPLE 158

2-Diethanolamino-8-furfuryloxy-4-(1oxido-thiomorpholino)pyrimido[5,4-d]pyrimidine This compound was prepared analogous to Example 4 from 2-chloro-8-furfuryloxy-4-(1-oxido-thiomorpholino)pyrimido[5,4-d]pyrimidine (melting point: 183°–185° C.) and diethanolamine.
Melting point: 198°–200° C. (dioxane).

EXAMPLE 159

8-(3-Ethoxy-propoxy)-2-diethanolamino-4-(1-oxidothiomorpholino)-pyrimido[5,4-d]pyrimidine This compound was prepared analogous to Example 4 from 8-(3-ethoxy-propoxy)-2-chloro-4-(1-oxido-thiomorpholino)pyrimido[5,4-d]pyrimidine (melting point: 130°-133° C.) and diethanolamine.

Melting point: 131°-133° C. (ethyl acetate).

EXAMPLE 160

2-Diethanolamino-8-(4-methyl-benzyloxy)-4-(1-oxido-thiomorpholino)-pyrimido[5,4-d]pyrimidine This compound was prepared analogous to Example 4 from 2-chloro-8-(4-methyl-benzyloxy)-4-(1-oxido-thiomorpholino)-pyrimido[5,4-d]pyrimidine (melting point: 178°-180° C.) and diethanolamine.

Melting point: 171°-173° C. (methanol).

EXAMPLE 161

2-Diethanolamine-8-(4-fluoro-benzyloxy)-4-(1-oxido-thiomorpholino)-pyrimido[5,4-d]pyrimidine This compound was prepared analogous to Example 4 from 2-chloro-8-(4-fluoro-benzyloxy)-4-(1-oxido-thiomorpholino)-pyrimido[5,4-d]pyrimidine (melting point: 226°-228° C.) and diethanolamine.

Melting point: 186°-188° C. (ethanol).

EXAMPLE 162

8-(4-Chloro-benzyloxy)-2-diethanolamino-4-(1-oxido-thiomorpholino) pyrimido[5,4-d]pyrimidine This compound was prepared analogous to Example 4 from 2-chloro-8-(4-chloro-benzyloxy)-4-(1-oxido-thiomorpholino)-pyrimido[5,4-d]pyrimidine (melting point: 214°-216° C.) and diethanolamine.

Melting point: 198°-200° C. (ethyl acetate/methanol).

EXAMPLE 163

2-Diethanolamino-8-(2,4-dichloro-benzyloxy)-4-(1-oxidothiomorpholino)-pyrimido[5,4-d]pyrimidine This compound was prepared analogous to Example 4 from 2-chloro-8-(2,4-dichloro-benzyloxy)-4-(1-oxido-thiomorpholino)-pyrimido[5,4-d]pyrimidine (melting point: 249°-251° C.) and diethanolamine.

Melting point: 208°-210° C. (ethanol/ethyl acetate).

EXAMPLE 164

2-Diethanolamino-8-(2-methoxy-benzyloxy)-4-(1-oxidothiomorpholino)-pyrimido[5,4-d]pyrimidine This compound was prepared analogous to Example 4 from 2-chloro-8-(2-methoxy-benzyloxy)-4-(1-oxido-thiomorpholino)-pyrimido[5,4-d]pyrimidine (melting point: 223°-225° C.) and diethanolamine.

Melting point: 174°-176° C. (ethyl acetate/methanol).

EXAMPLE 165

2-Diethanolamino-8-(4-methoxy-benzyloxy)-4-(1-oxidothiomorpholino)-pyrimido[5,4-d]pyrimidine This compound was prepared analogous to Example 4 from 2-chloro-8-(4-methoxy-benzyloxy)-4-(1-oxido-thiomorpholino)-pyrimido[5,4-d]pyrimidine (melting point: 184°-186° C.) and diethanolamine.

Melting point: 147°-149° C. (ethyl acetate/methanol).

EXAMPLE 166

2-Diethanolamino-8-(3,4-dimethoxy-benzyloxy)-4-(1-oxidothiomorpholino)-pyrimido[5,4-d]pyrimidine This compound was prepared analogous to Example 4 from 2-chloro-8-(3,4-dimethoxy-benzyloxy)-4-(1-oxidothiomorpholino)-pyrimido[5,4-d]pyrimidine (melting point: 171°-173° C.) and diethanolamine.

Melting point: 157°-159° C. (dioxane).

EXAMPLE 167

2-Diethanolamino-8-(3,4-methylenedioxy-benzyloxy)-4-(1-oxido-thiomorpholino)-pyrimido[5,4-d]pyrimidine This compound was prepared analogous to Example 4 from 2-chloro-8-(3,4-methylenedioxy-benzyloxy)-4-(1-oxidothiomorpholino)-pyrimido[5,4-d]pyrimidine (melting point: 216°-218° C.) and diethanolamine.

Melting point: 186°-187° C. (dioxane).

EXAMPLE 168

2-(2-Hydroxyethyl-amino)-8-(4-methyl-benzylthio)-4-(1-oxido-thiomorpholino)-pyrimido[5,4-d]pyrimidine This compound was prepared analogous to Example 1 from 2-chloro-8-(4-methyl-benzylthio)-4-(1-oxido-thiomorpholino)-pyrimido[5,4-d]pyrimidine (melting point: 262°-264° C.) and 2-hydroxyethyl-amine.

Melting point: 189°-191° C. (dioxane).

EXAMPLE 169

8-(4-Fluoro-benzylthio)-2-(2-hydroxyethyl-amino)-4-(1-oxido-thiomorpholino)-pyrimido[5,4-d]pyrimidine This compound was prepared analogous to Example 1 from 2-chloro-8-(4-fluoro-benzylthio)-4-(1-oxido-thiomorpholino)-pyrimido[5,4-d]pyrimidine (melting point: 192°-194° C.) and 2-hydroxyethyl-amine.

Melting point: 222°-224° C. (ethanol/dioxane).

EXAMPLE 170

8-(2-chloro-benzylthio)-2-(2-hydroxyethyl-amino)-4-(1-oxido-thiomorpholino)-pyrimido[5,4-d]pyrimidine This compound was prepared analogous to Example 1 from 2-chloro-8-(2-chloro-benzylthio)-4-(1-oxidothiomorpholino)-pyrimido[5,4-d]pyrimidine (melting point: 203°-206° C.) and 2-hydroxyethyl-amine.

Melting point: 205°-207° C. (ethanol/dioxane).

EXAMPLE 171

8-(4-Chloro-benzylthio)-2-(2-hydroxyethyl-amino)-4-(1-oxido-thiomorpholino)-pyrimido[5,4-d]pyrimidine This compound was prepared analogous to Example 1 from 2-chloro-8-(4-chloro-benzylthio)-4-(1-oxido-thiomorpholino)-pyrimido[5,4-d]pyrimidine (melting point: 232°-234° C.) and 2-hydroxyethyl-amine.

Melting point: 222°-224° C. (ethanol/dioxane).

EXAMPLE 172

8-(2,4-dichloro-benzylthio)-2-(2-hydroxyethyl-amino)-4-(1-oxido-thiomorpholino)-pyrimido[5,4-d]pyrimidine This compound was prepared analogous to Example 1 from 2-chloro-8-(2,4-dichloro-benzylthio)-4-(1-oxido-thiomorpholino)-pyrimido[5,4-d]pyrimidine (melting point: 227°-229° C.) and 2-hydroxyethyl-amine.

Melting point: 254°-256° C. (dioxane).

EXAMPLE 173

8-(3,4-Dichloro-benzylthio)-2-(2-hydroxyethyl-amino)-4-(1-oxido-thiomorpholino)-pyrimido[5,4-d]pyrimidine This compound was prepared analogous to Example 1 from 2-chloro-8-(3,4-dichloro-benzylthio)-4-(1-oxido-thiomorpholino)-pyrimido[5,4-d]pyrimidine (melting point: 210°–212° C.) and 2-hydroxyethyl-amine.

Melting point: 211°–213° C. (ethanol/dioxane).

EXAMPLE 174

2-(2-Hydroxyethyl-amino)-4-(1-oxido-thiomorpholino)-8-(3-trifluoromethylbenzyl-thio)-pyrimido[5,4-d pyrimidine This compound was prepared analogous to Example 1 from 2-chloro-4-(1-oxido-thiomorpholino)-8-(trifluoromethylbenzyl-thio)-pyrimido[5,4-d]pyrimidine (melting point: 211°–213° C.) and 2-hydroxyethyl-amine.

Melting point: 199°–201° C. (ethyl acetate).

EXAMPLE 175

2-(2-Hydroxyethyl-amino)-8-(4-methoxybenzyl-thio)-4-(1-oxido-thiomorpholino)-pyrimido[5,4-d]pyrimidine This compound was prepared analogous to Example 1 from 2-chloro-8-(4-methoxybenzyl-thio)-4-(1-oxido-thiomorpholino)-pyrimido[5,4-d]pyrimidine (melting point: 217°–219° C.) and 2-hydroxyethyl-amine.

Melting point: 204°–206° C. (ethanol/dioxane).

EXAMPLE 176

8-(3,4-Dimethoxybenzyl-thio)-2-(2-hydroxyethyl-amino)-4-(1-oxido-thiomorpholino)-pyrimido[5,4-d]pyrimidine This compound was prepared analogous to Example 1 from 2-chloro-8-(3,4-dimethoxybenzyl-thio)-4-(1-oxidothiomorpholino)-pyrimido[5,4-d]pyrimidine (melting point: 186°–188° C.) and 2-hydroxyethyl-amine.

Melting point: 198°–200° C. (ethanol).

EXAMPLE 177

2-(2-Hydroxyethyl-amino)-8-(3,4-methylenedioxybenzyl-thio)-4-(1-oxido-thiomorpholino) pyrimido[5,4-d]pyrimidine This compound was prepared analogous to Example 1 from 2-chloro-8-(3,4-methylenedioxybenzyl-thio)-4-(1-oxido-thiomorpholino)-pyrimido[5,4-d]pyrimidine (melting point: 229°–231° C.) and 2-hydroxyethyl-amine.

Melting point: 215°–217° C. (ethanol/dioxane).

EXAMPLE 178

2-(2-Hydroxyethyl-amino)-8-(α-methyl-4-methylthiobenzylthio)-4-(1-oxido-thiomorpholino)-pyrimido[5,4-d]pyrimidine This compound was prepared analogous to Example 1 from 2-chloro-8-(α-methyl-4-methylthiobenzyl-thio)-4(1-oxido-thiomorpholino)-pyrimido[5,4-d]pyrimidine (melting point: 200°–202° C.) and 2-hydroxyethyl-amine.

Melting point: 150°–152° C. (ethanol).

EXAMPLE 179

2-(2-Hydroxyethyl-amino)-8-(α-methyl-4-methylthiobenzylthio)-4-morpholino-pyrimido[5,4-d]pyrimidine This compound was prepared analogous to Example 1 from 2-chloro-8-(α-methyl-4-methylthiobenzyl-thio)-pyrimido [5,4-d]pyrimidine (melting point: 146°–149° C.) and 2-hydroxyethyl-amine.

Melting point: 142°–144° C. (ethanol).

EXAMPLE 180

8-(3-Chlorobenzyl-thio)-2-(2-hydroxyethyl-amino)-4-(1-oxido-thiomorpholino)-pyrimido[5,4-d]pyrimidine This compound was prepared analogous to Example 1 from 2-chloro-8-(3-chloro-benzyl-thio)-4-(1-oxidothiomorpholino)-pyrimido[5,4-d]pyrimidine (melting point: 179°–182° C.) and 2-hydroxyethyl-amine.

Melting point: 200°–202° C. (ethanol/dioxane).

EXAMPLE 181

8-(2,6-Dichlorobenzyl-thio)-2-(2-hydroxyethyl-amino)-4-(1-oxido-thiomorpholino)-pyrimido[5,4-d]pyrimidine This compound was prepared analogous to Example 1 from 2-chloro-8-(2,6-dichlorobenzyl-thio)-4-(1-oxido-thiomorpholino)-pyrimido[5,4-d]pyrimidine (melting point: 215°–218° C.) and 2-hydroxyethyl-amine.

Melting point: 203°–206° C. (ethanol/dioxane).

EXAMPLE 182

2-(2-Hydroxyethyl-amino)-8-(3-nitrobenzyl-thio)-4-(1-oxido-thiomorpholino)-pyrimido[5,4-d]pyrimidine This compound was prepared analogous to Example 1 from 2-chloro-8-(3-nitrobenzyl-thio)-4-(1-oxido-thiomorpholino)-pyrimido[5,4-d]pyrimidine (melting point: 233°–235° C.) and 2-hydroxyethyl-amine.

Melting point: 207°–209° C. (ethanol/dioxane).

EXAMPLE 183

2-[N-Ethyl-N-(2-hydroxy-ethyl)-amino]-8-benzylthio-4-(1-oxido-thiomorpholino)-pyrimido[5,4-d]pyrimidine This compound was prepared analogous to Example 1 from 8-benzylthio-2-chloro-4-(1-oxido-thiomorpholino)pyrimido[5,4-1]pyrimidine (melting point: 188°–190° C.) and N-ethyl-N-(2-hydroxy-ethyl)-amine.

Melting point: 182°–184° C. (methanol).

EXAMPLE 184

8-Benzylthio-2-[N-(2-hydroxy-ethyl)-isopropylamino]-4-(1-oxido-thiomorpholino)-pyrimido[5,4-d]pyrimidine This compound was prepared analogous to Example 1 from 8-benzylthio-2-chloro-4-(1-oxido-thiomorpholino)pyrimido[5,4-d]-pyrimidine and N-(2-hydroxyethyl)isopropylamine.

Melting point: 188°–190° C. (ethyl acetate).

EXAMPLE 185

8-Benzylthio-2-[N-butyl-N-(2-hydroxy-ethyl)-amino]-4-(1-oxido-thiomorpholino)-pyrimido[5,4-d]pyrimidine This compound was prepared analogous to Example 1 from 8-benzylthio-2-chloro-4-(1-oxido-thiomorpholino)pyrimido[5,4-d]pyrimidine and N-butyl-N-(2-hydroxyethyl)amine.

Melting point: 111°–113° C. (ethyl acetate).

EXAMPLE 186

8-Benzylthio-2-[(1,1-dimethyl-2-hydroxy-ethyl)-amino]-4-(1-oxido-thiomorpholino)-pyrimido[5,4-d]pyrimidine This compound was prepared analogous to Example 1 from 8-benzylthio-2-chloro-4-(1-oxido-thiomorpholino)pyrimido[5,4-d]pyrimidine (melting point: 188°–190° C.) and 2-amino-2-methyl-propanol in dioxane by refluxing for 24 hours.

Melting point: 186°–188° C. (ethanol).

EXAMPLE 187

8-Benzylthio-2-[(2,2-dimethyl-3-hydroxy-propyl)-amino]-4-(1-oxido-thiomorpholino)-pyrimido[5,4-d]pyrimidine This compound was prepared analogous to Example 1 from 8-benzylthio-2-chloro-4-(1-oxido-thiomorpholino)pyrimido[5,4-d]pyrimidine and 3-amino-2,2-dimethyl-propanol.

Melting point: 181°–183° C. (ethanol).

EXAMPLE 188

8-Benzylthio-2-[2-(2-hydroxy-ethoxy)-ethyl-amino]-4-(1-oxido-thiomorpholino)-pyrimido[5,4-d]pyrimidine This compound was prepared analogous to Example 1 from 8-benzylthio-2-chloro-4-(1-oxido-thiomorpholino)-pyrimido[5,4-d]pyrimidine and 2-(2-hydroxyethoxy)-ethylamine.

Melting point: 153°–155° C. (ethanol).

EXAMPLE 189

8-Benzylthio-4-(1-oxido-thiomorpholino)-2-(trans-4-hydroxycyclohexyl-amino)pyrimido[5,4-d]pyrimidine This compound was prepared analogous to Example 1 from 8-benzylthio-2-chloro-4-(1-oxido-thiomorpholino)pyrimido[5,4-d]pyrimidine and trans-4-hydroxy-cyclohexylamine.

Melting point: 227°–229° C. (dioxane).

EXAMPLE 190

8-(2-Ethylhexyl-amino)-2-(2-hydroxyethyl-amino)-4-(1-oxido-thiomorpholino)-pyrimido[5,4-d]pyrimidine This compound was prepared analogous to Example 2 from 8-(2-ethylhexyl-amino)-2-chloro-4-(1-oxido-thiomorpholino)-pyrimido[5,4-d]pyrimidine (melting point: 118°–120° C.) and 2-hydroxyethyl-amine.

Melting point: 140°–142° C. (ethyl acetate).

EXAMPLE 191

8-(2-Chloro-anilino)-2-(2-hydroxyethyl-amino)-4-(1-oxido-thiomorpholino)-pyrimido[5,4-d]pyrimidine This compound was prepared analogous to Example 3 from 2-chloro-8-(2-chloro-anilino)-4-(1-oxido-thiomorpholino)-pyrimido[5,4-d]pyrimidine (melting point: 263°–265° C.) and 2-hydroxyethyl-amine.

Melting point: 216°–218° C. (dioxane).

EXAMPLE 192

8-(2,6-dichlorobenzyl-amino)-2-(2-hydroxyethyl-amino)-4-(1-oxido-thiomorpholino)-pyrimido[5,4-d]pyrimidine This compound was prepared analogous to Example 2 from 2-chloro-8-(2,6-dichlorobenzyl-amino)-4-(1-oxidothiomorpholino)-pyrimido[5,4-d]pyrimidine (melting point: 239°–241° C.) and 2-hydroxyethylamine.

Melting point: 199°–201° C. (ethanol).

EXAMPLE 193

2-(2-Hydroxyethyl-amino)-4-(1-oxido-thiomorpholino)-8-(1,2,3,4-tetrahydro-quinolino)-pyrimido[5,4-d]pyrimidine This compound was prepared analogous to Example 3 from 2-chloro-4-(1-oxido-thiomorpholino)-8-(1,2,3,4-tetrahydro-quinolino)-pyrimido[5,4-d]pyrimidine (melting point: 198°–199° C.) and 2-hydroxyethyl-amine at about 100° C.

Melting point: 186°–188° C. (methanol).

EXAMPLE 194

2-(2-Hydroxyethyl-amino)-4-(1-oxido-thiomorpholino)-8-(1,2,3,4-tetrahydro-isoquinolino)-pyrimido[5,4-d]pyrimidine This compound was prepared analogous to Example 2 from 2-chloro-4-(1-oxido-thiomorpholino)-8-(1,2,3,4-tetrahydro-isoquinolino)-pyrimido[5,4-d]pyrimidine (melting point: 164°–166° C.) and 2-hydroxyethylamine.

Melting point: 143°–145° C. (methanol).

EXAMPLE 195

8-Benzylamino-2-[N-(2-hydroxy-ethyl)-methylamino]-4-(1-oxido-thiomorpholino)-pyrimido[5,4-d]pyrimidine This compound was prepared analogous to Example 2 from 8-benzylamino-2-chloro-4-(1-oxido-thiomorpholino)pyrimido[5,4-d]pyrimidine (melting point: 232°–233° C.) and N-(2-hydroxy-ethyl)-methylamine in dioxane under reflux.

Melting point: 171°–173° C. (methahol).

EXAMPLE 196

2-[N-Ethyl-N-(2-hydroxyethyl-amino)]-8-benzylamino-4-(1-oxido-thiomorpholino)-pyrimido[5,4-d]pyrimidine This compound was prepared analogous to Example 2 from 8-benzylamino-2-chloro-4-(1-oxido-thiomorpholino)pyrimido[5,4-d]pyrimidine and N-ethyl-N-(2-hydroxyethyl)-amine.

Melting point: 175°–177° C. (ethyl acetate).

EXAMPLE 197

8-Benzylamino-2-[N-(2-hydroxy-ethyl)-propylamino]-4-(1-oxido-thiomorpholino)-pyrimido[5,4-d]pyrimidine This compound was prepared analogous to Example 2 from 8-benzylamino-2-chloro-4-(1-oxido-thiomorpholino)pyrimido[5,4-d]pyrimidine and N-(2-hydroxyethyl)propylamine.

Melting point: 143°–145° C. (ethyl acetate).

EXAMPLE 198

8-Benzylamino-2-[2-(2-hydroxy-ethoxy)-ethylamino]-4-(1-oxido-thiomorpholino)-pyrimido[5,4-d]pyrimidine This compound was prepared analogous to Example 2 from 8-benzylamino-2-chloro-4-(1-oxido-thiomorpholino)pyrimido[5,4-d]pyrimidine (melting point: 232°–233° C.) and 2-(2-hydroxy-ethoxy)-ethylamine.

Melting point: 128°–130° C. (methanol).

EXAMPLE 199

8-Benzylamino-2-(4-hydroxy-piperidino)-4-(1-oxidothiomorpholino)pyrimido[5,4-d]pyrimidine This compound was prepared analogous to Example 2 from 8-benzylamino-2-chloro-4-(1-oxido-thiomorpholino)pyrimido[5,4-d]pyrimidine and 4-hydroxy-piperidine.

Melting point: 225°–226° C. (dioxane).

EXAMPLE 200

8-Benzylamino-4-(1-oxido-thiomorpholino)-2-(trans-4-hydroxy-cyclohexyl-amino)-pyrimido[5,4-d]pyrimidine This compound was prepared analogous to Example 3 from 8-benzylamino-2-chloro-4-(1-oxido-thiomorpholino)pyrimido[5,4-d]pyrimidine and trans-4-hydroxycyclohexylamine.

Melting point: 200°–202° C. (methanol).

EXAMPLE 201

8-Benzylamino-2-cyclohexylamino-4-(1-oxido-thiomorpholino)pyrimido[5,4-d]pyrimidine This compound was prepared analogous to Example 2 from 8-benzylamino-2-chloro-4-(1-oxido-thiomorpholino)pyrimido[5,4-d]pyrimidine and cyclohexylamine.

Melting point: 174°–176° C. (methanol).

EXAMPLE 202

2-Diethanolamino-8-(2-fluoro-benzyloxy)-4-(1-oxido-thiomorpholino)-pyrimido[5,4-d]pyrimidine This compound was prepared analogous to Example 4 from 2-chloro-8-(2-fluoro-benzyloxy)-4-(1-oxidothiomorpholino)-pyrimido[ 5,4-d]pyrimidine (melting point: 212°–214° C.) and diethanolamine.

Melting point: 150°–152° C. (ethyl acetate).

EXAMPLE 203

2-Diethanolamine-8-(3-fluoro-benzyloxy)-4-(1-oxido-thiomorpholino)-pyrimido[5,4-d]pyrimidine This compound was prepared analogous to Example 4 from 2-chloro-8-(3-fluoro-benzyloxy)-4-(1-oxido-thiomorpholino)-pyrimido[5,4-d]pyrimidine (melting point: 206°–208° C.) and diethanolamine.

Melting point: 190°–192° C. (dioxane).

EXAMPLE 204

2-Diethanolamino-8-(2-chloro-benzyloxy)-4-(1-oxido-thiomorpholino)-pyrimido[5,4-d]pyrimidine This compound was prepared analogous to Example 4 from 2-chloro-8-(2-chloro-benzyloxy)-4-(1-oxido-thiomorpholino)-pyrimido[5,4-d]pyrimidine (melting point: 213°–215° C.) and diethanolamine.

Melting point: 209°–211° C. (ethyl acetate/methanol).

EXAMPLE 205

2-Diethanolamino-8-(2,6-dichloro-benzyloxy)-4-(1-oxidothiomorpholino)-pyrimido[5,4-d]pyrimidine This compound was prepared analogous to Example 4 from 2-chloro-8-(2,6-dichloro-benzyloxy)-4-(1-oxido-thiomorpholino)-pyrimido[5,4-d]pyrimidine (melting point: 237°–239° C.) and diethanolamine.

Melting point: 206°–208° C. (methanol/ethyl acetate).

EXAMPLE 206

2-Diethanolamino-8-(3,4-dichloro-benzyloxy)-4-(1-oxidothiomorpholino)-pyrimido[5,4-d]pyrimidine This compound was prepared analogous to Example 4 from 2-chloro-8-(3,4-dichloro-benzyloxy)-4-(1-oxido-thiomorpholino)-pyrimido[5,4-d]pyrimidine (melting point: 211°–213° C.) and diethanolamine.

Melting point: 205°–207° C. (dioxane).

EXAMPLE 207

2-Diethanolamine-8-(2,2-dimethyl-propoxy)-4-(1-oxidothiomorpholino)-pyrimido[5,4-d]pyrimidine This compound was prepared analogous to Example 4 from 2-chloro-8-(2,2-dimethyl-propoxy)-4-(1-oxidothiomorpholino)-pyrimido[5,4-d]-pyrimidine (melting point: 231°–232° C.) and diethanolamine.

Melting point: 171°–173° C. (ethyl acetate).

EXAMPLE 208

8-Benzyloxy-2-(N-methyl-3-picolylamino)-4-(1-oxido-thiomorpholino)-pyrimido[5,4-d]pyrimidine This compound was prepared analogous to Example 4 from 8-benzyloxy-2-chloro-4-(1-oxido-thiomorpholino)pyrimido[5,4-d]pyrimidine (melting point: 227°–229° C.) and N-methyl-3-picolylamine.

Melting point: 168°–170° C. (ethyl acetate/methanol).

The compounds of the present invention, that is, those embraced by formula I above and their non-toxic, pharmacologically acceptable acid addition salts, have useful pharmacodynamic properties. More particularly, they exhibit primarily antithrombotic activity in warmblooded animals. In addition, they exhibit hypotensive, cardiotonic and PDE-inhibiting activities and an inhibiting effect on the aggregation of cancer cells suspended in the blood stream.

The antithrombotic property and the acute toxicity of the compounds of the present invention were determined by the test methods described below, and the results of these tests for a few representative species of the genus are shown in the tables, where A = 2-(2-Hydroxyethyl-amino)-4-(1-oxido-thiomorpholino)-8-propylthio-pyrimido[5,4-d[pyrimidine, B = 8-Cyclohexylthio-2-(2-hydroxyethyl-amino)-4-(1-oxido-thiomorpholino)-pyrimido[5,4-d]pyrimidine, C = 8-Benzylthio-2-(2-hydroxyethyl-amino)-4-(1-oxido-thiomorpholino)-pyrimido[5,4-d]pyrimidine, D = 8-Benzylthio-2-diethanolamine-4-(1-oxido-thiomorpholino)-pyrimido[5,4-d]pyrimidine, E = 8-Benzylthio-2-[N-(2-hydroxy-ethyl)-N-(2-methoxyethyl)-amino]-4-(1-oxido-thiomorpholino)-pyrimido[5,4-d]pyrimidine, F = 2-(2-Hydroxyethyl-amino)-8-(α-methyl-4-methylthiobenzyl-thio)-4-(1-oxido-thiomorpholino)-pyrimido[5,4-d]pyrimidine, G = 8-Furfurylthio-2-(2-hydroxyethyl-amino)-4-(1-oxidothiomorpholino)-pyrimido[5,4-d-pyrimidine, H = 8-(N-Ethyl-butylamino)-2-(2-hydroxyethyl-amino)-4(1-oxido-thiomorpholino)-pyrimido[5,4-d]pyrimidine, I = 2-(2-Hydroxyethyl-amino)-4-(1-oxido-thiomorpholino)8-(L-1-phenyl-ethylamino)-pyrimido[5,4-d]pyrimidine, K = 8-(4-Chlorobenzyl-amino)-2-(2-hydroxyethyl-amino)4-(1-oxido-thiomorpholino)-pyrimido[5,4-d]pyrimidine, L = 2-Diethanolamino-4-(1-oxido-thiomorpholino)-8-piperidino-pyrimido[5,4-d]pyrimidine,
M = 2-Diethanolamino-8-isopentoxy-4-(1-oxido-thiomorpholino)-pyrimido[5,4-d]pyrimidine,
N = 8-Benzyloxy-2-diethanolamino-4-(1-oxido-thiomorpholino)-pyrimido[5,4-d]pyrimidine,
O = 8-Benzyloxy-2-[N-(2-hydroxy-ethyl)-N-(2-methoxy-ethyl)amino]4-(1-oxido-thiomorpholino)-pyrimido[5,4-d]pyrimidine, and
P = 2-Diethanolamino-4-(1-oxido-thiomorpholino)-8-(3-phenylpropoxy)-pyrimido[5,4-d]pyrimidine.

1. Anti-thrombotic activity

Thrombocyte aggregation was measured according to the method of Born and Cross [J. Physiol. 170, 397 (1964)] in platelet-rich plasma of healthy test persons. To inhibit coagulation, the blood was mixed with sodium citrate in a volume ration of 1:10.

Collagen-induced aggregation

After addition of the aggregation-inducing substance, the rate of decrease in optical density of the platelet suspension is measured photometrically and recorded. The rate of aggregation was determined from the angle of inclination of the density curve. The point on the curve at which there was the greatest translucence served for calculating the optical density.

The quantity of collagen was chosen as small as possible, but sufficient so that an irreversible reaction was obtained. Commercial collagen of Hormonchemie, Munich, was used. Before the collagen was added, the plasma was incubated for 10 minutes with the test substance at 37° C.

An $EC_{50}$ corresponding to a 50% change in the optical density with respect to aggregation inhibition was calculated graphically from the measurement values obtained.

The following table shows the results:

TABLE I

| Compound | $EC_{50}$ μmol/liter |
|---|---|
| A | 0.31 |
| B | 0.048 |
| C | 0.021 |
| D | 0.062 |
| E | 0.052 |
| F | 0.029 |
| G | 0.052 |
| H | 0.3 |
| I | 0.028 |
| K | 0.28 |
| L | 0.69 |
| M | 0.46 |
| N | 0.23 |
| O | 0.3 |
| P | 0.36 |

2. Acute toxicity

The acute toxicity of the test compounds was determined on groups of 6 to 10 mice after oral administration of a dose of 250 mg/kg (observation time: 14 days). For this purpose, the substances were suspended in 2% methyl cellulose, some water was subsequently added and the test substance was administered to the conscious animals by esophageal tube.

The following table shows the results:

TABLE II

| Compound | Toxicity in mg/kg p.o. |
|---|---|
| A | >250 (0 out of 6 animals died) |
| B | >250 (0 out of 10 animals died) |
| C | >250 (0 out of 10 animals died) |
| D | >250 (0 out of 10 animals died) |
| E | >250 (0 out of 10 animals died) |
| F | >250 (0 out of 6 animals died) |
| G | >250 (0 out of 6 animals died) |
| H | >250 (0 out of 6 animals died) |
| K | >250 (0 out of 10 animals died) |
| L | >250 (0 out of 10 animals died) |
| M | >250 (0 out of 6 animals died) |
| N | >250 (0 out of 10 animals died) |
| O | >250 (0 out of 6 animals died) |
| P | >250 (0 out of 6 animals died) |

In view of these pharmacological properties, the compounds of the formula I and their non-toxic, pharmacologically acceptable acid addition salts are useful for the prophylaxis of thrombo-embolic diseases such as coronary infarction, cerebral infarction, so-called transient ischaemic attacks or amaurosis fugax, and for the prophylaxis of arterio-sclerosis.

For pharmaceutical purposes the compounds of the present invention are administered to warm-blooded animals perorally, parenterally or rectally as active ingredients in customary dosage unit compositions, that is, compositions in dosage unit form consisting essentially of an inert pharmaceutical carrier and one effectice dosage unit of the active ingredient, such as tablets, coated pills, capsules, wafers, powders, solutions, suspensions, emulsions, syrups, suppositories and the like. One effective dosage unit of the compounds according to the present invention is from 0.0014 to 0.29 mgm/kg body weight, preferably 0.007 to 0.07 mgm/kg body weight, 2 to 4 times daily.

The following examples illustrate a few pharmaceutical dosage unit compositions comprising a compound of the present invention as an active ingredient and represent the best modes contemplated of using the invention. The parts are parts by weight unless otherwise specified:

EXAMPLE 209

Coated tablets

The tablet core is compounded from the following ingredients:

| | |
|---|---|
| 8-Benzylthio-2-(2-hydroxyethyl-amino)-4-(1-oxido-thiomorpholino)-pyrimido[5,4-d]pyrimidine | 1.0 parts |
| Lactose | 30.0 parts |
| Corn starch | 14.5 parts |
| Polyvinyl pyrrolidone | 4.0 parts |
| Magnesium stearate | parts |
| Total | 50.0 parts |

Preparation:

The active ingredient, the lactose and the corn starch are intimately admixed with each other, the mixture is uniformly moistened with an aqueous solution of the polyvinyl pyrrolidone, and the moist mass is granulated by passing it through a 1 mm-mesh screen. The granulate is dried, again passed through the screen, admixed with the magnesium stearate, and the composition is compressed into 50 mgm tablet cores which are subsequently coated with a thin sugar shell. Each coated tablet is an oral dosage unit composition containing 1 mgm of the active ingredient.

EXAMPLE 210

Tablets

The tablet composition is compounded from the following ingredients:

| | | |
|---|---:|---|
| 8-Benzylthio-2-(2-hydroxyethyl-amino)-4-(1-oxido-thiomorpholino)-pyrimido[5,4-d]pyrimidine | 2.0 | parts |
| Lactose | 29.0 | parts |
| Corn starch | 14.5 | parts |
| Polyvinyl pyrrolidone | 4.0 | parts |
| Magnesium stearate | parts | |
| Total | 50.0 | parts |

Preparation:

The ingredients are compounded as described in Example 209, and the composition is compressed into 50 mgm-tablets, each of which is an oral dosage unit composition containing 2 mgm of the active ingredient.

EXAMPLE 211

Suppositories

The suppository composition is compounded from the following ingredients:

| | | |
|---|---:|---|
| 8-Benzylthio-2-(2-hydroxyethyl-amino)-4-(1-oxide-thiomorpholino)-pyrimido[5,4-d]pyrimidine | 5.0 | parts |
| Suppository base (e.g. cocoa butter) | 1695.0 | parts |
| Total | 1700.0 | parts |

Preparation:

The suppository base is melted and cooled to 38° C. and the pulverized active ingredient is homogeneously distributed therein with the aid of an immersion homogenizer. 1700 mgm-portions of the composition are poured at 35° C. into cooled suppository molds and allowed to harden therein. Each suppository is a rectal dosage unit composition containing 5 mgm of the active ingredient.

EXAMPLE 212

Aqueous suspension

The suspension is compounded from the following ingredients:

| | | |
|---|---:|---|
| 8-Benzylthio-2-(2-hydroxyethyl-amino)-4-(1-oxido-thiomorpholino)-pyrimido[5,4-d]pyrimidine | 0.04 | parts |
| Carboxymethyl cellulose | 0.1 | parts |
| Methyl p-hydroxy-benzoate | 0.05 | parts |
| Propyl p-hydroxy-benzoate | 0.01 | parts |
| Cane sugar | 10.0 | parts |
| Glycerol | 5.0 | parts |
| Sorbitol solution 70% | 20.0 | parts |
| Flavoring | 0.3 | parts |
| Distilled water q.s. ad | 100.0 | parts by vol. |

Preparation:

The distilled water is heated to 70° C. The methyl and propyl p-hydroxy-benzoates as well as the glycerol and the carboxymethyl cellulose are dissolved therein while stirring. The mixture is cooled to room temperature, and the active ingredient is added while stirring and dispersed homogeneously. After the sugar, sorbitol solution and flavoring have been added and dissolved, the suspension is evacuated while stirring to remove air. 5 ml of the suspension are an oral dosage unit composition containing 2 mgm of the active ingredient.

EXAMPLE 213

Hypodermic solution

The solution is compounded from the following ingredients:

| | | |
|---|---:|---|
| 2-Diethanolamino-4-(1-oxido-thiomorpholino)-8-piperidino-pyrimido[5,4-d]pyrimidine | 1.0 | parts |
| Hydrochloric acid, 0.01 N | 300.0 | parts by vol. |
| Sodium chloride | 18.0 | parts |
| Water for injection q.s. ad | 2000.0 | parts by vol. |

Preparation:

In a calibrated vessel, the active ingredient base is suspended in the water for injection purposes and is completely dissolved by heating and dropwise addition of the hydrochloric acid. After filtering through a diaphragm filter, the solution is filled into 2 cc-ampules which are then sterilized in an autoclave and sealed. The contents of each ampule are an injectable dosage unit composition containing 1 mgm of the active ingredient.

Any one of the other compounds embraced by formula I or a non-toxic, pharmacologically acceptable acid addition salt thereof may be substituted for the particular active ingredient in Examples 209 through 213. Likewise, the amount of active ingredient in these illustrative examples may be varied to achieve the dosage unit range set forth above, and the amounts and nature of the inert pharmaceutical carrier ingredients may be varied to meet particular requirements.

While the present invention has been illustrated with the aid of certain specific embodiments thereof, it will be readily apparent to others skilled in the art that the invention is not limited to these particular embodiments, and that various changes and modifications may be made without departing from the spirit of the invention or the scope of the appended claims.

We claim:

1. A compound of the formula

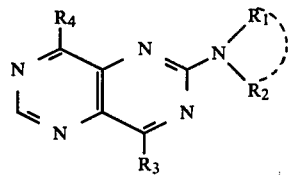

wherein $R_1$ is straight or branched alkyl of 2 to 8 carbon atoms, optionally substituted in the 2- to 8-position by 1 to 5 hydroxyls; alkyl of 2 to 4 carbon atoms mono-substituted in the 2-, 3- or 4-position by alkoxy of 1 to 3 carbon atoms, amino, (alkyl of 1 to 3 carbon atoms-)amino, di(alkyl of 1 to 3 carbon atoms)-amino; methyl; or pyridylmethyl;

$R_2$ is hydrogen; alkyl of 1 to 3 carbon atoms; or alkyl of 2 to 3 carbon atoms mono-substituted in the 2- or 3-position by hydroxyl or alkoxy of 1 to 3 carbon atoms; or $R_1$ and $R_2$, together with each other and the nitrogen atom to which they are attached, are imidazolyl; thiomorpholino; 1-oxido-thiomorpholino; piperidino; or mono-substituted piperidino, where the substituent is hydroxyl, alkoxy of 1 to 3 carbon atoms, hydroxy-(alkyl of 1 to 3 carbon atoms), alkoxycarbonyl of 2 to 4 carbon atoms, amino, (alkanoyl of 1 to 3 carbon atoms)-amino, aminocarbonyl, (alkyl of 1 to 3 carbon atoms)-amino or di(alkyl of 1 to 3 carbon atoms)-amino;

$R_3$ is thiomorpholino, 1-oxidothiomorpholino or 1,1-dioxido-thiomorpholino, each of which is optionally mono- or di-substituted by one or two alkyls of 1 to 3 carbon atoms;

$R_4$ is

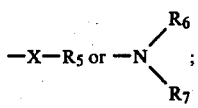

X is sulfur or oxygen;

$R_5$ is alkyl of 1 to 4 carbon atoms, optionally mono-substituted by phenyl or in the 2-, 3- or 4-position by hydroxyl, di(alkyl of 1 to 3 carbon atoms)-amino, alkoxy of 1 to 3 carbon atoms or alkoxycarbonyl of 2 to 4 carbon atoms; when X is sulfur, also phenyl; where each of the aforementioned phenyl moieties may optionally be methylenedioxy-substituted, mononitro-substituted, or mono- or di-substituted by alkyl of 1 to 3 carbon atoms, alkoxy of 1 to 3 carbon atoms, (alkyl of 1 to 3 carbon atoms)thio, trifluoromethyl and/or halogen; alkyl of 5 to 8 carbon atoms; cycloalkyl of 5 to 7 carbon atoms; furfuryl; indanyl; or naphthylmethyl;

$R_6$ is hydrogen; alkyl of 1 to 4 carbon atoms; or alkyl of 2 to 4 carbon atoms monosubstituted in the 2-, 3- or 4-position by hydroxyl or alkoxy of 1 to 3 carbon atoms; and $R_7$ is hydrogen; alkyl of 1 to 4 carbon atoms; phenyl-(alkyl of 1 to 4 carbon atoms); phenyl; where each of the aforementioned phenyl moieties may optionally be methylenedioxy-substituted or mono- or di-substituted by alkyl of 1 to 3 carbon atoms, alkoxy of 1 to 3 carbon atoms, (alkyl of 1 to 3 carbon atoms)-thio, trifluoromethyl and/or halogen; alkyl of 5 to 8 carbon atoms; cycloalkyl of 5 to 7 carbon atoms; alkyl of 2 to 8 carbon atoms mono-substituted in the 2- to 8-position by hydroxyl, alkoxy of 1 to 3 carbon atoms or hydroxy-(alkoxy of 1 to 3 carbon atoms); cyclohexylmethyl; hydroxycyclohexyl; furfuryl; or pyridyl-methyl; or $R_6$ and $R_7$, together with each other and the nitrogen atoms to which they are attached, are alkyleneimino of 4 to 7 carbon atoms, optionally monohydroxy-substituted or mono- or di-substituted by alkyl of 1 to 3 carbon atoms; tetrahydropyridino; tetrahydroquinolino; or tetrahydroisoquinolino;

or a non-toxic, pharmacologically acceptable acid addition salt thereof.

2. A compound of claim 1, where $R_1$ is alkyl of 2 to 8 carbon atoms, optionally substituted in the 2- to 8-positions by up to 5- hydroxyls; 2-methoxy-ethyl; 2-amino-ethyl; 2-diethylamino-ethyl; methyl; or pyridylmethyl;

$R_2$ is hydrogen; or alkyl of 1 to 3 carbon atoms optionally mono-substituted in the 2- or 3-position by hydroxyl or methoxy; or $R_1$ and $R_2$, together with each other and the nitrogen atoms to which they are attached, are piperidino, optionally mono-substituted by hydroxyl, methoxy, hydroxymethyl, dimethylamino, acetamino, aminocarbonyl or ethoxycarbonyl; 1-oxido-thiomorpholino; or imidazolyl;

$R_3$ is thiomorpholino, 1-oxido-thiomorpholino or 1,1-dioxidothiomorpholino;

$R_4$ is alkoxy of 1 to 8 carbon atoms; phenyl-(alkoxy-of 1 to 4 carbon atoms); cyclohexyloxy; alkylthio of 1 to 8 carbon atoms; phenyl-(alkylthio of 1 to 4 carbon atoms); phenylthio; where the phenyl moieties of afore-mentioned benzyloxy, benzylthio or phenylthio groups may be methylene dioxy-substituted, mononitro-substituted or mono- or di-substituted by methyl, hydroxyl, methoxy, methylthio, trifluoromethyl, fluorine, chlorine or bromine; cyclohexylthio; 2-hydroxyethyl-thio; 2-diethylamino-ethyl-thio; ethoxycarbonyl-methyl-thio; α-methyl-methylthiobenzyl-thio; naphthyl-methyl-thio; furfuryl-thio; indanyl; or

$R_6$ is hydrogen; alkyl of 1 to 4 carbon atoms; or alkyl of 2 to 3 carbon atoms substituted in the 2- or 3-position by methoxy; and $R_7$ is hydrogen; alkyl of 1 to 8 carbon atoms, hydroxy-(alkyl of 2 to 8 carbon atoms); alkyl of 2 to 3 carbon atoms mono-substituted in the 2- or 3-position by methoxy, ethoxy or hydroxyethoxy; phenyl-(alkyl of 2 carbon atoms), optionally mono- or di-methoxy-substituted on the phenyl moiety; cyclohexyl; hydroxy-cyclohexyl; cyclohexyl-methyl; 3-phenyl-propyl; 4-phenyl-butyl; furfuryl; pyridylmethyl, phenyl, optionally methylenedioxy-substituted or mono- or di-substituted by methyl, hydroxyl, methoxy, ethoxy, methylthio, trifluoromethyl, fluorine and/or chlorine; or benzyl, optionally methylenedioxy-substituted or mono- or di-substituted by methyl, hydroxyl, methoxy, ethoxy, methylthio, trifluoromethyl, fluorine and/or chlorine on the phenyl moiety; or $R_6$ and $R_7$, together with each other and the nitrogen atom to which they are attached, are pyrrolidino, piperidino, methyl-piperidino, ethyl-piperidino, dimethyl-piperidino, hydroxy-piperidino, hexamethyleneimino, heptamethyleneimino, tetrahydropyridino, tetrahydroquinolino or tetrahydroisoquinolino;

or a non-toxic, pharmacologically acceptable acid addition salt thereof.

3. A compound of claim 2, where $R_1$, $R_2$ and $R_4$ have the meanings defined in claim 2, and $R_3$ is oxido-thiomorpholino, or a non-toxic, pharmacologically acceptable acid addition salt thereof.

4. A compound of claim 1 where $R_1$ is alkyl of 2 to 5 carbon atoms, optionally mono- or di-hydroxy-substituted or mono-methoxy-substituted in the 2- to 5-position;

$R_2$ is hydrogen or 2-hydroxy-ethyl;

R₃ is 1-oxido-thiomorpholino;

R₄ is alkoxy of 1 to 6 carbon atoms, phenyl-(alkoxy of 1 to 3 carbon atoms), alkylthio of 1 to 6 carbon atoms, phenyl-(alkylthio of 1 to 3 carbon atoms), cyclohexylthio or

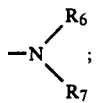

R₆ is hydrogen or alkyl of 1 to 4 carbon atoms; and

R₇ is alkyl of 2 to 5 carbon atoms; mono-hydroxy-substituted alkyl of 2 to 5 carbon atoms; or mono-phenyl-substituted alkyl of 1 to 4 carbon atoms; where the phenyl moiety of aforementioned benzylamino, benzyloxy or benzylthio groups may be mono- or di-substituted by fluorine, chlorine and/or methoxy; or R₆ and R₇, together with each other and the nitrogen atoms to which they are attached, are pyrrolidino, piperidino or hexamethyleneimino;

or a non-toxic, pharmacologically acceptable acid addition salt thereof.

5. A compound of claim 1, which is 8-benzylthio-2-(2-hydroxyethyl-amino)-4-(1-oxido-thiomorpholino)-pyrimido[5,4-d]pyrimidine or a non-toxic, pharmacologically acceptable acid addition salt thereof.

6. A compound of claim 1, which is 2-(2-hydroxyethyl-amino)-4-(1-oxido-thiomorpholino)-8-(L-1-phenylethylamino)-pyrimido[5,4-d]pyrimidine or a non-toxic, pharmacologically acceptable acid addition salt thereof.

7. A compound of claim 1, which is 8-benzylamino-2-(2-hydroxyethyl-amino)-4-(1-oxido-thiomorpholino)-pyrimido[5,4-d]pyrimidine or a non-toxic, pharmacologically acceptable acid addition salt thereof.

8. An antithrombotic pharmaceutical composition consisting essentially of an inert pharmaceutical carrier and an effective antithrombotic amount of a compound of claim 1.

9. The method of preventing or relieving thromboses, arteriosclerosis and metastasis formation in a warm-blooded animal in need thereof, which comprises per-orally, parenterally or rectally administering to said animal an effective amount of a compound of claim 1.

* * * * *

UNITED STATES PATENT AND TRADEMARK OFFICE
CERTIFICATE OF CORRECTION

PATENT NO. : 4,478,833
DATED : October 23, 1984
INVENTOR(S) : JOSEF ROCH ET AL.

It is certified that error appears in the above-identified patent and that said Letters Patent is hereby corrected as shown below:

Column 3, line 3: "zyloxy" should read -- zyloxy, --.

Column 15, line 27: "pyrinido" should read -- pyrimido --.

Column 18, line 29: "[5,4-d] (melting" should read -- [5,4-d]pyrimidine (melting --.

Column 25, line 30: "dine from" should read -- dine This compound was prepared analogous to Example 3 from --.

Column 38, line 38: "(methahol)" should read -- methanol --.

Column 42, line 56: "parts" should read -- 0.5 parts --.

Column 43, line 15: "parts" should read -- 0.5 parts --.

Signed and Sealed this

Ninth Day of July 1985

[SEAL]

Attest:

DONALD J. QUIGG

Attesting Officer    Acting Commissioner of Patents and Trademarks